(12) United States Patent
Poor

(10) Patent No.: US 12,036,138 B2
(45) Date of Patent: Jul. 16, 2024

(54) MEDICAL STENTS

(71) Applicants: STRYKER CORPORATION, Kalamazoo, MI (US); STRYKER EUROPEAN OPERATIONS LIMITED, Carrigtwohill (IE)

(72) Inventor: Michael T. Poor, Kalamazoo, MI (US)

(73) Assignees: Stryker Corporation, Kalamazoo, MI (US); Stryker European Operations Limited, Carrigtwohill (IE)

(*) Notice: Subject to any disclaimer, the term of this patent is extended or adjusted under 35 U.S.C. 154(b) by 196 days.

(21) Appl. No.: 17/390,294

(22) Filed: Jul. 30, 2021

(65) Prior Publication Data

US 2023/0035464 A1 Feb. 2, 2023

(51) Int. Cl.
*A61F 2/90* (2013.01)
*A61F 2/966* (2013.01)

(52) U.S. Cl.
CPC .......... *A61F 2/90* (2013.01); *A61F 2/966* (2013.01); *A61F 2250/0096* (2013.01)

(58) Field of Classification Search
CPC .... A61F 2/90; A61F 2/966; A61F 2250/0096; A61F 2002/9505; A61F 2002/9501; A61F 2002/9528; A61F 2002/9665
See application file for complete search history.

(56) References Cited

U.S. PATENT DOCUMENTS

| | | | |
|---|---|---|---|
| 2006/0025847 A1* | 2/2006 | Parker | A61F 2/91 623/1.15 |
| 2006/0241741 A1* | 10/2006 | Lootz | A61F 2/91 623/1.34 |
| 2007/0055348 A1 | 3/2007 | Pryor | |

(Continued)

FOREIGN PATENT DOCUMENTS

| | | |
|---|---|---|
| CN | 1988857 A | 6/2007 |
| CN | 101642397 A | 2/2010 |
| CN | 102481186 | 5/2012 |
| CN | 102711677 | 10/2012 |
| CN | 105636557 A | 6/2016 |
| CN | 109937023 A | 6/2019 |

(Continued)

OTHER PUBLICATIONS

Foreign Search Report for CN Patent Appln. No. 2021112850261 dated Nov. 5, 2021.

(Continued)

*Primary Examiner* — Elizabeth Houston
*Assistant Examiner* — James R McGinnity
(74) *Attorney, Agent, or Firm* — Vista IP Law Group, LLP

(57) ABSTRACT

A stent configured for implantation in a body lumen, includes: a tubular structure having a first end, a second end opposite from the first end, and a tubular body extending between the first and second ends, the tubular body comprising a plurality of elongate portions defining a porosity for the stent, at least one of the elongate portions having a zig-zag configuration, the first end of the tubular structure having a plurality of crown elements disposed circumferentially with respect to a longitudinal axis of the tubular structure, the crown elements forming a crown configuration for the first end of the tubular body; and a plurality of tabs coupled to the first end of the tubular structure; wherein a number of the crown elements is higher than a number of the tabs; wherein the tabs are coupled to only a subset, and not all, of the crown elements.

20 Claims, 17 Drawing Sheets

(56) References Cited

U.S. PATENT DOCUMENTS

| | | | |
|---|---|---|---|
| 2007/0266542 A1* | 11/2007 | Melsheimer | A61B 90/39 623/1.34 |
| 2010/0211161 A1* | 8/2010 | Dreher | A61F 2/91 623/1.34 |
| 2013/0110253 A1* | 5/2013 | Gill | A61F 2/04 623/23.68 |
| 2014/0277380 A1 | 9/2014 | Vogel et al. | |
| 2020/0188095 A1 | 6/2020 | Liu | |
| 2020/0237495 A1* | 7/2020 | Jackson | A61F 2/90 |
| 2020/0268535 A1* | 8/2020 | Carpenter | A61F 2/915 |
| 2021/0000625 A1* | 1/2021 | Ta | A61F 2/915 |
| 2021/0007837 A1* | 1/2021 | Haldis | A61F 2/01 |

FOREIGN PATENT DOCUMENTS

| | | |
|---|---|---|
| CN | 109937024 | 6/2019 |
| CN | 109952078 | 6/2019 |
| CN | 113081421 A | 7/2021 |
| WO | WO2021011819 A1 | 1/2021 |

OTHER PUBLICATIONS

Search Report for current application performed on behalf of the Chinese Patent Authority dated Sep. 26, 2021.

\* cited by examiner

MEDICAL STENTS

FIELD

The present disclosure relates generally to medical devices and intravascular medical procedures and, more particularly, to stents and methods of delivering and using the same.

BACKGROUND

Rupture of non-occlusive cerebrovascular lesions, such as intracranial saccular aneurysms or arterio-venous fistulae, is a major cause of stroke. Rupture of an aneurysm causes subarachnoid hemorrhage in which blood from a ruptured vessel spreads over the surface of the brain. About 2.5% of the United States population (4 million Americans) have an unruptured aneurysm. About 100,000 of these people suffer a subarachnoid hemorrhage each year. The disease is devastating, often affecting healthy people in their 40's and 50's, with about half of the rupture victims succumbing within a month, and with half of the survivors becoming seriously disabled as a result of the initial hemorrhage or of a delayed complication.

Neurovascular arteries are generally quite small, having diameters ranging from 2.0 to 4.0 mm in the Circle of Willis, 2.5 to 5.5 mm in the cavernous segment of the internal carotid artery, 1.5 to 3.0 mm in vessels of the distal anterior circulation, and 2.0 to 4.0 mm in the posterior circulation. The incidence of aneurysm varies with the location, with 55% occurring in the Circle of Willis, 30% in the internal carotid, 10% in the distal anterior circulation, and 5% in the posterior circulation.

Screening for these lesions and preventing rupture will lead to better clinical outcomes and lower costs. Non-invasive treatments for ruptured and unruptured lesions are preferred over surgical interventions due to lower costs, lower mortality and morbidity, and patient preference.

Another type of vascular abnormality is atherosclerosis. Atherosclerosis is a disease in which plaque builds up inside a blood vessel. The plaque may cause obstruction of blood flow. Plaques may also rupture, causing acute occlusion of the blood vessel by clot. Often times, atherosclerosis has no symptoms, until a plaque ruptures or the buildup of plaque is severe enough to block blood flow.

One possible treatment for neurovascular aneurysms and other small-vessel abnormalities (e.g., atherosclerosis) involves placement of a stent at the site of weakened or damaged vessels. Such a treatment, however, involves several formidable challenges. First, assuming the stent is placed at the target site via a small-diameter catheter, it would be desirable for the stent to be flexible enough to allow movement of the catheter along a typically tortuous vascular path, which may involve a number of sharp turns or bends in and through small-diameter vessels, i.e., vessels having diameters in the 2-8 mm range. Second, when the stent is released, it may be desirable for the stent to be capable of expanding from the inner-lumen diameter of the catheter to a diameter somewhat equal to or greater than that of the vessel at the target site (e.g., having an expansion ratio of at least twofold). Third, it would be desirable for the stent to provide adequate structural support at the target site to maintain the vessel in a slightly expanded-diameter state. In particular, the stent design should minimize the risk of metal fatigue as the stent is placed between its expanded and compressed forms. Fourth, it would be desirable for the stent to provide a low profile and a surface that minimizes the formation of blood thrombi. Finally, it may be desirable that the stent provide an open-network skeleton that allows for delivery of additional agents, e.g., vaso-occlusive coils, drugs, etc., through the stent.

In some cases, it may be desirable to form a body of the stent using zigzag elements. However, such zigzag elements may be twisted or bent outward during and/or after delivery of the stent, thereby making it difficult to deploy the stent out of a delivery catheter, and increasing the risk of the stent damaging a wall of a blood vessel. The zigzag elements may also deform and jam into each other during delivery of the stent. In addition, the zigzag elements may form a crown configuration at opposite ends of the stent. These zigzag elements may also cause injury to vessel wall and/or make deployment of the stent out of a delivery catheter difficult. Thus, it may be advantageous to provide a stent formed by zigzag elements, which does not have the above issues.

It would therefore be valuable to provide an intravascular stent, particular one for use in treating neurovascular aneurysms and other vascular abnormalities (e.g., atherosclerosis), that provides one or more of the advantages and features mentioned above.

SUMMARY

A stent configured for implantation in a body lumen, includes: a tubular structure having a first end, a second end opposite from the first end, and a tubular body extending between the first end and the second end, the tubular body comprising a plurality of elongate portions defining a porosity for the stent, at least one of the elongate portions having a zig-zag configuration, the first end of the tubular structure having a plurality of crown elements disposed circumferentially with respect to a longitudinal axis of the tubular structure, the crown elements forming a crown configuration for the first end of the tubular body; and a plurality of tabs coupled to the first end of the tubular structure, the tabs being disposed circumferentially with respect to the longitudinal axis of the tubular structure; wherein the tabs are configured to move radially away from the longitudinal axis of the tubular structure in correspondence with a radial expansion of the tubular structure; wherein a number of the crown elements is higher than a number of the tabs; wherein the tabs are coupled to only a subset, and not all, of the crown elements; and wherein the stent has a delivery configuration when confined inside a delivery catheter, and wherein one of the tabs is coupled to one of the crown elements, and is disposed in front of an adjacent one of the crown elements when the stent is in the delivery configuration.

Optionally, the number of crown elements is 3 or higher.

Optionally, the number of crown elements is 8, and the number of tabs is 3.

Optionally, a ratio that is the number of crown elements divided by the number of tabs is a non-integer.

Optionally, the number of the crown elements is an even number, and the number of the tabs is an odd number, or vice versa.

Optionally, the tabs comprise marker tabs.

Optionally, one of the crown elements comprises a bent of one of the elongate portions.

Optionally, one of the tabs comprises a curvilinear structure, wherein the curvilinear structure is curved with respect to the longitudinal axis, and comprises a tab-opening defined by circumferential parts of the curvilinear structure.

Optionally, the tabs are configured to circumferentially move apart from each other in correspondence with a radial expansion of the tubular structure.

Optionally, the tabs comprise a first tab having at least four sides, wherein the at least four sides comprise a first side and a second side opposite from the first side, wherein the first side of the first tab partly forms a tip of the stent, and wherein the second side of the first tab is perpendicular to the longitudinal axis of the tubular structure.

Optionally, one of the crown elements is coupled to the second side of the first tab at a location on the second side that is away from a center of the second side.

Optionally, the stent has an expanded configuration for implantation in the body lumen, and wherein the stent is biased to the expanded configuration.

Optionally, the porosity of the stent is between fifty and ninety-five percent (50-95%) when the stent is in the expanded configuration.

Optionally, the elongate portions comprise a first zigzag portion and a second zigzag portion.

Optionally, one of the elongate portions comprises a zigzag portion forming a ring element, the ring element having a first ring end, and a second ring end opposite from the first ring end, wherein the first ring end has a first set of peaks disposed circumferentially around the longitudinal axis of the tubular structure, and wherein the second ring end has a second set of peaks disposed circumferentially around the longitudinal axis of the tubular structure.

Optionally, the peaks in the first set are flat or are rectilinear.

Optionally, one of the peaks in the first set is formed by an elongate member, and has a surface with a surface area that is at least 20% larger than that of a reference peak formed only by a hypothetical bending of the elongate member.

Optionally, the subset of the crown elements is attached to the tabs at respective off-centered locations that are different among the respective tabs.

An assembly includes the stent and the delivery catheter, wherein the stent is located in a lumen of the delivery catheter.

Optionally, the assembly further includes a plunger located in the lumen of the delivery catheter, wherein the plunger is slidable relative to the delivery catheter, and is located proximal with respect to the stent.

A stent configured for implantation in a body lumen, includes: a tubular structure having a first end, a second end opposite from the first end, and a tubular body extending between the first end and the second end, the tubular body comprising a plurality of elongate portions defining a porosity for the stent, the first end of the tubular structure having a plurality of crown elements disposed circumferentially with respect to a longitudinal axis of the tubular structure, the crown elements forming a crown configuration for the first end of the tubular body; and a plurality of tabs coupled to the first end of the tubular structure, the tabs being disposed circumferentially with respect to the longitudinal axis of the tubular structure; wherein the tabs are configured to move radially away from the longitudinal axis of the tubular structure in correspondence with a radial expansion of the tubular structure; wherein the elongate portions comprise a first zigzag portion forming a first ring element, the first ring element having a first ring end, and a second ring end opposite from the first ring end, wherein the first ring end of the first ring element has a first set of peaks disposed circumferentially around the longitudinal axis of the tubular structure, and wherein the second ring end of the first ring element has a second set of peaks disposed circumferentially around the longitudinal axis of the tubular structure; and wherein the peaks in the first set are flat or are rectilinear.

Optionally, the elongate portions comprise a second zigzag portion forming a second ring element, the second ring element having a first ring end and a second ring end opposite from the first ring end of the second ring element, wherein the first ring end of the second ring element has a set of peaks disposed circumferentially around the longitudinal axis of the tubular structure, and wherein the peaks of the second ring element are flat or are rectilinear.

Optionally, the set of peaks of the second ring element faces towards the second set of peaks of the first ring element.

Optionally, a number of the crown elements is higher than a number of the tabs; and wherein the tabs are coupled to only a subset, and not all, of the crown elements.

Optionally, the number of crown elements is 3 or higher.

Optionally, the number of crown elements is 8, and the number of tabs is 3.

Optionally, a ratio that is the number of crown elements divided by the number of tabs is a non-integer.

Optionally, the number of the crown elements is an even number, and the number of the tabs is an odd number, or vice versa.

Optionally, the tabs comprise marker tabs.

Optionally, one of the crown elements comprises a bent of one of the elongate portions.

Optionally, one of the tabs comprises a curvilinear structure, wherein the curvilinear structure is curved with respect to the longitudinal axis, and comprises a tab-opening defined by circumferential parts of the curvilinear structure.

Optionally, the tabs are configured to circumferentially move apart from each other in correspondence with a radial expansion of the tubular structure.

Optionally, the tabs comprise a first tab having at least four sides, wherein the at least four sides comprise a first side and a second side opposite from the first side, wherein the first side of the first tab partly forms a tip of the stent, and wherein the second side of the first tab is perpendicular to the longitudinal axis of the tubular structure.

Optionally, one of the crown elements is coupled to the second side of the first tab at a location on the second side that is away from a center of the second side.

Optionally, the stent has a delivery configuration sized for introduction into a lumen of a delivery catheter, and an expanded configuration for implantation in the body lumen, and wherein the stent is biased to the expanded configuration.

Optionally, the porosity of the stent is between fifty and ninety-five percent (50-95%) when the stent is in the expanded configuration.

Optionally, one of the peaks in the first set is formed by an elongate member, and has a surface with a surface area that is at least 20% larger than that of a reference peak formed only by a hypothetical bending of the elongate member.

An assembly includes the stent and a delivery catheter, wherein the stent is located in a lumen of the delivery catheter.

Optionally, the assembly further includes a plunger located in the lumen of the delivery catheter, wherein the plunger is slidable relative to the delivery catheter, and is located proximal with respect to the stent.

Other and further aspects and features will become apparent from the ensuing detailed description in view of the accompanying figures.

DETAILED DESCRIPTION

Figure 1:
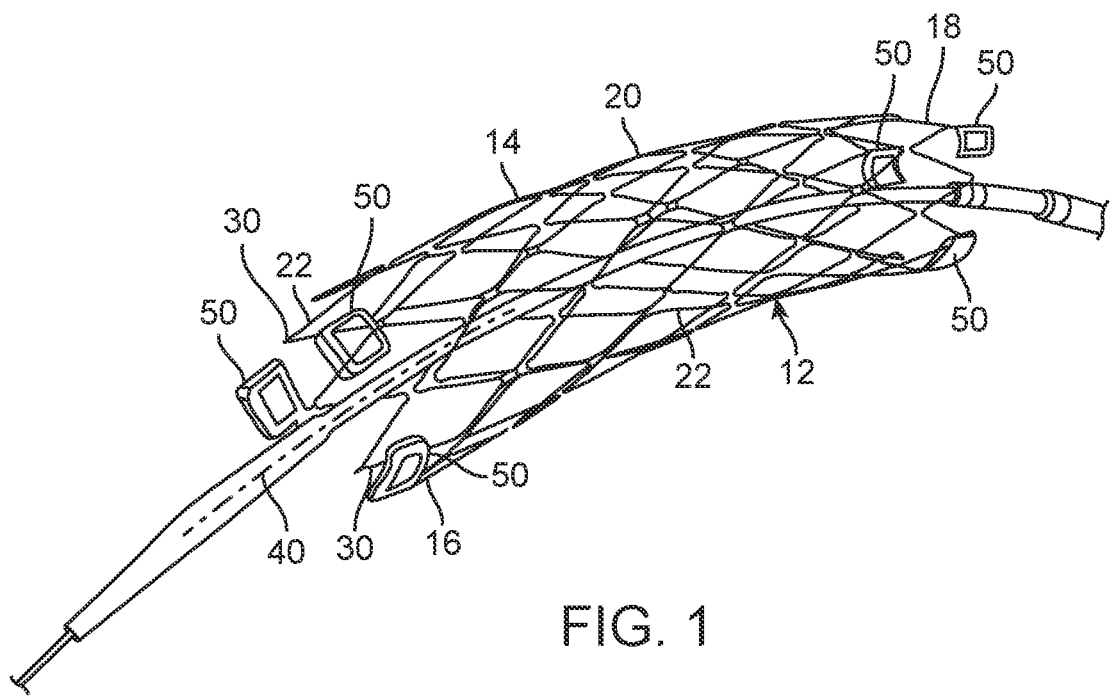
FIG. 1 illustrates an assembly that includes a sent and a delivery catheter.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various features are described hereinafter with reference to the figures. The figures may or may not be drawn to scale. Elements of similar structures or functions are represented by like reference numerals throughout the figures. It should also be understood that the figures are only intended to facilitate the description of the features, and are not intended as an exhaustive description of the claimed inventions, or as a limitation on the scope thereof, which is defined only by the appended claims and their equivalents.

In addition, a device or a method needs not have all of the depicted features, and a feature, aspect or advantage described in conjunction with a particular device or method is not necessarily limited to that device or method, but can be practiced in other device or method, even if not so illustrated.

FIG. 1 illustrates a stent 12 configured for implantation in a body lumen. The stent 12 includes a tubular structure 14 having a first end 16, a second end 18 opposite from the first end 16, and a tubular body 20 extending between the first end 16 and the second end 18. The tubular body 20 comprises a plurality of elongate portions 22 defining a porosity for the stent 12. At least one of the elongate portions 22 having a zig-zag configuration. The first end 16 of the tubular structure 14 has a plurality of crown elements 30 disposed circumferentially with respect to a longitudinal axis 40 of the tubular structure 14. The crown elements 30 forms a crown configuration for the first end 16 of the tubular structure 14. The stent 12 also has a plurality of tabs 50 coupled to the first end 16 of the tubular structure 14, the tabs 50 being disposed circumferentially with respect to the longitudinal axis 40 of the tubular structure 14. The tabs 50 are configured to move radially away from the longitudinal axis 40 of the tubular structure 14 in correspondence with a radial expansion of the tubular structure 14. A number of the crown elements 30 is higher than a number of the tabs 50. The tabs 50 are coupled to only a subset, and not all, of the crown elements 30.

Figure 2A:
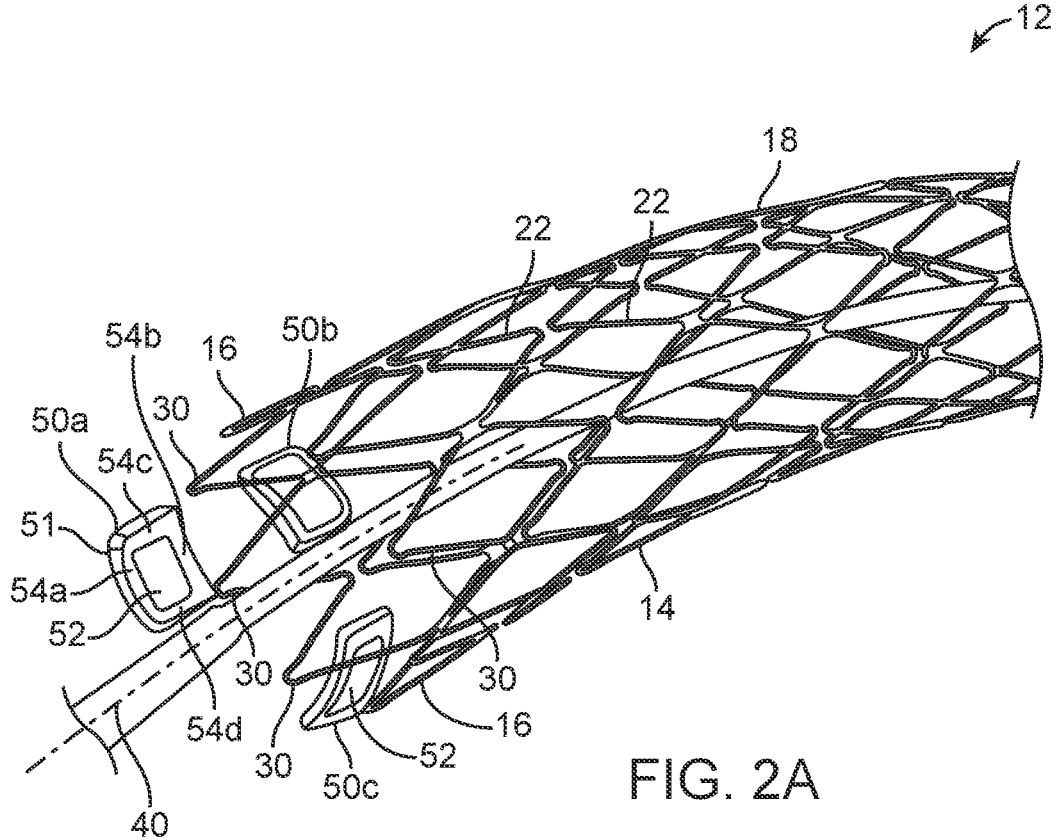
FIG. 2A illustrates a distal portion of the stent of FIG. 1.
Figure 2B:
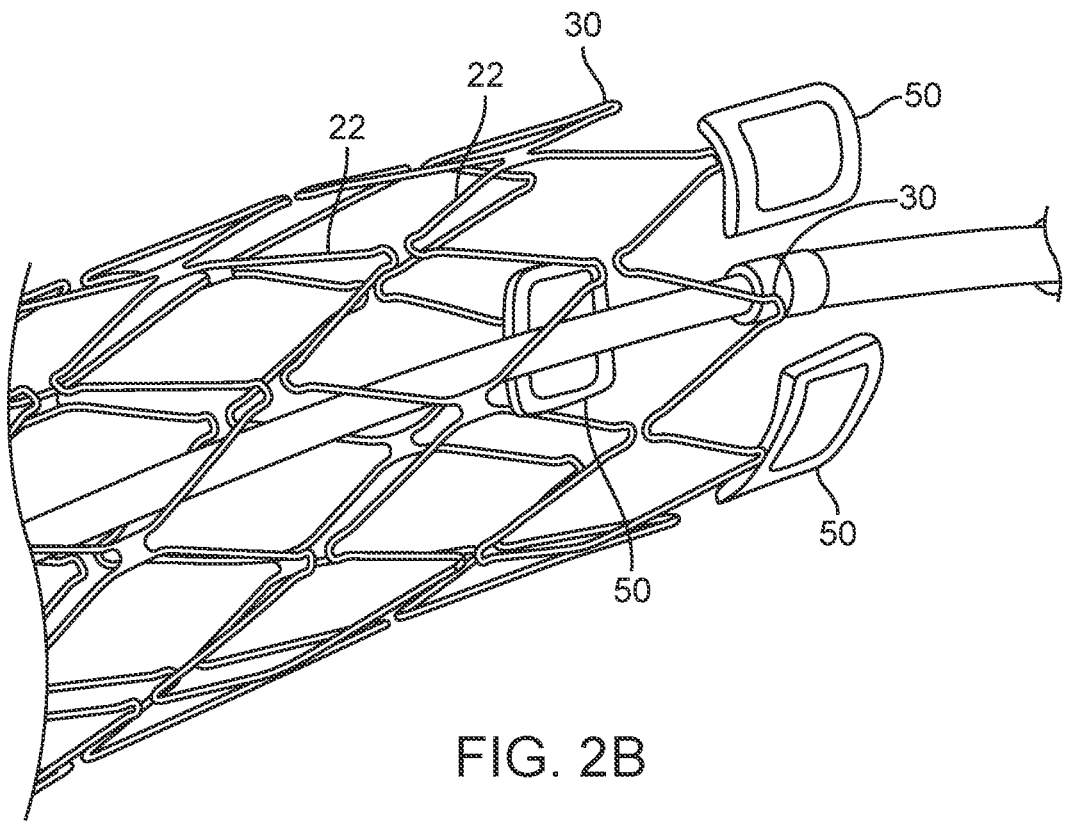
FIG. 2B illustrates a proximal portion of the stent of FIG. 1.

FIG. 2A illustrates a distal portion of the stent of FIG. 1. FIG. 2B illustrates a proximal portion of the stent of FIG. 1. As shown in these figures, opposite ends 16, 18 of the tubular structure 14 have respective sets of tabs 50 coupled thereto. In some cases, the tabs 50 is made from a material that is radiopaque, which allows visualization of the stent 12 during delivery and placement of the stent 12 inside the patient. Thus, the tabs 50 are marker tabs. In other cases the tabs 50 may not be radiopaque, and the tabs 50 may not be marker tabs.

In some cases, each of the tabs 50 has a curvilinear structure 51, wherein the curvilinear structure is curved with respect to the longitudinal axis 40 of the tubular structure 14. Each tab 50 also has a tab-opening 52 defined by circumferential parts (i.e., sides 54a-54d) of the curvilinear structure. In other cases, each tab 50 may have a solid core, and may not include any tap-opening 52.

As shown in FIG. 2A, the first end 16 of the tubular structure 14 is coupled to three tabs 50a-50c (i.e., a first tab 50a, a second tab 50b, and a third tab 50c). The first tab 50a has at least four sides 54a-54d, wherein the at least four sides 54a-54d comprise a first side 54a and a second side 54b opposite from the first side 54a, wherein the first side 54a of the first tab 50a partly forms a tip of the stent 12, and wherein the second side 54b of the first tab 50a is perpendicular to the longitudinal axis 40 of the tubular structure 14. One of the crown elements 30 is shown being coupled to the second side 54b of the first tab 50a at a location on the second side 54b that is away from a center of the second side 54b.

Figure 3A:
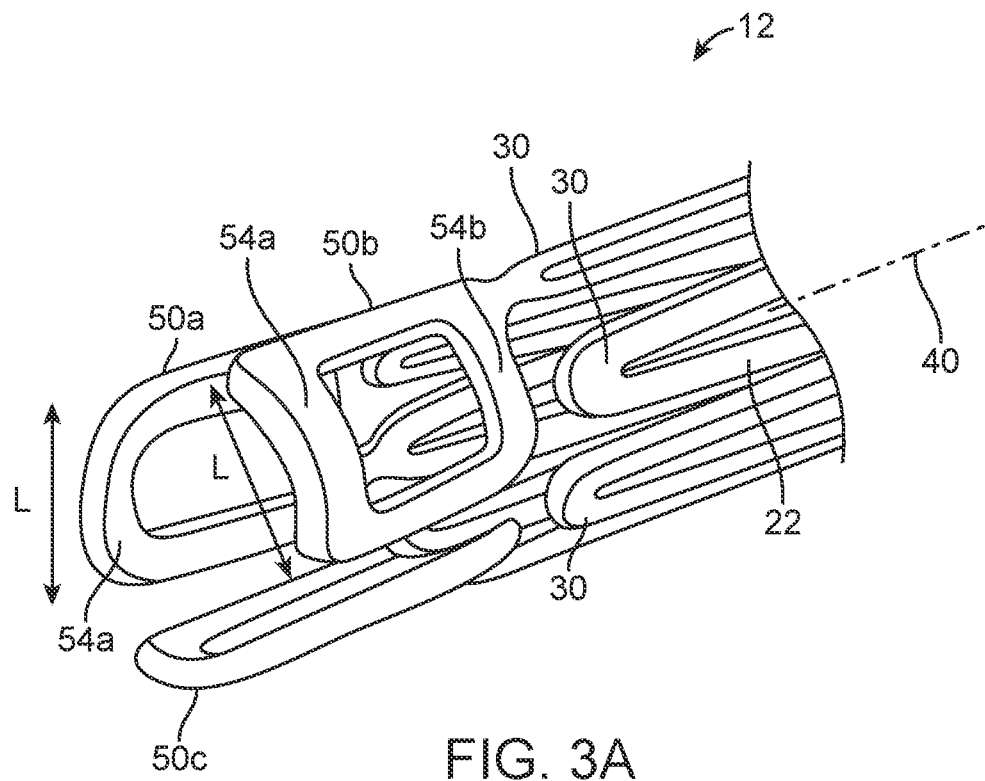
FIG. 3A illustrates the distal portion of the stent of FIG. 1, particularly showing the stent in a non-expanded configuration.

FIG. 3A illustrates a distal portion of the stent 12 of FIG. 1, particular showing the stent 12 in a non-expanded configuration. The non-expanded configuration may be the delivery configuration assume by the stent 12 when the stent 12 is confined within a lumen of a delivery catheter. After the stent 12 is delivered out of the delivery catheter, the stent 12 assumes an expanded configuration for implantation in a body lumen (e.g., blood vessel) due to the stent 12 being biased to the expanded configuration. As shown in the figure, when the stent 12 is in the non-expanded configuration, the tabs 50a-50c are circumferentially and radially closer to each other. Also, each tab 50 has a transverse length L (e.g., a length of side 54a/54b that is perpendicular to the longitudinal axis 40) that is longer than a circumferential width of the crown element 30. This configuration is advantageous because it allows a part of the tab 50 to be placed in front of an adjacent crown element 30 when the stent 12 is in its delivery configuration inside the deliver catheter, thereby preventing the adjacent crown element 30 from poking against a vessel wall during delivery of the stent 12. The tabs 50 are configured to circumferentially move apart from each other in correspondence with a radial expansion of the tubular structure 14.

Figure 3B:
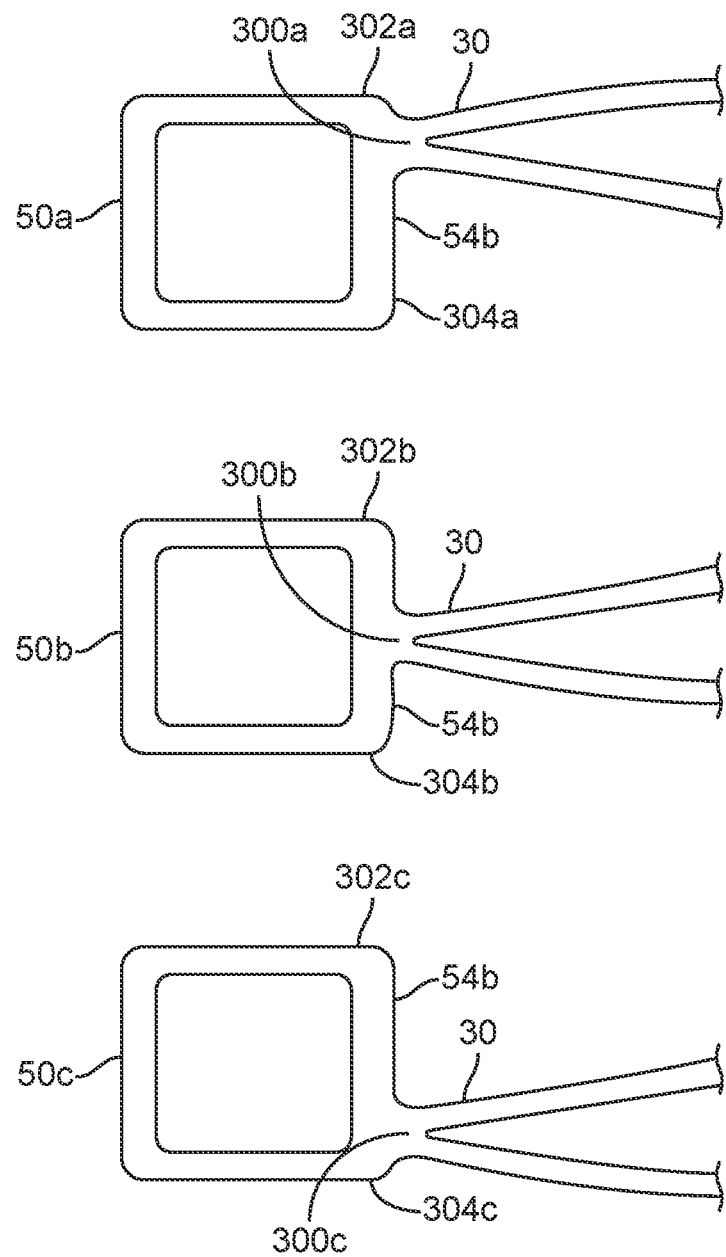
FIG. 3B illustrates crown elements coupled to respective tabs at different respective locations of the tabs.

In the illustrated example, the stent 12 has eight crown elements 30, and three tabs 50*a*-50*c*. The three tabs 50*a*-50*c* are placed circumferentially evenly around the axis 40 of the tubular structure 14. The eight crown elements 30 are also disposed circumferentially evenly around the axis 40 of the tubular structure 14. Because the number of crown elements 30 in the illustrated example cannot be easily divided by the number of tabs 50, in order to evenly couple the tabs 50 to the crown elements 30, the coupling between the tabs 50 and the crown elements 30 is achieved in an offset configuration. In such offset configuration, three of the eight crown elements 30 are coupled to respective tabs 50*a*-50*c* at locations of the tabs 50*a*-50*c* that are different from each other. For example, one of the crown elements 30 may couple to the side 54*b* of the first tab 50*a* at a location 300*a* on the side 54*b* that is closer to a first end 302*a* of the side 54*b* than to a second end 304*a* (opposite from the first end) of the side 54*b* (i.e., the crown element is coupled to the tab 50*a* at a location on the tab 50*a* that is off-centered—i.e., away from a center of a side of the tab 50*a*), another one of the crown elements 30 may couple to the side 54*b* of the second tab 50*b* at a location 300*b* (e.g., center) of the side 54*b* that is equal distance from the first end 302*b* and the second end 304*b*, and/or another one of the crown elements 30 may couple to the side 54*b* of the third tab 50*c* at a location 300*c* on the side 54*b* that is closer to a second end 304*c* of the side 54*b* than to the first end 302*c* (i.e., the crown element is coupled to the tab 50*c* at a location on the tab 50*c* that is off-centered—i.e., away from a center of a side of the tab 50*c*) (See FIG. 3B).

By using an offset configuration to couple the tabs 50 to the crown elements 30, the tabs 50 can be disposed circumferentially evenly while the stent 12 is constrained inside a delivery catheter. This allows for better tracking through the delivery catheter. For example, the offset or off-centered attachment locations for the tabs 50 (which may be different among the respective tabs 50) make it possible that an odd number of tabs can be disposed circumferentially evenly, while being attached to an even number of the crown elements 30. In some cases, a crown element 30 may be attached to a center of a side of a tab 50. In such cases, the attachment location may be characterized as having an off-centered value of zero. Accordingly, the term "off-centered attachment location" may refer to attachment location that is off-centered (having off-centered value >0), or attachment location that is centered (having off-centered value=0).

In the illustrated example, the tabs 50*a*-50*c* have the same shape and dimensions. In other cases, the tabs 50 may have different shapes and/or dimensions. For example, in other cases, the tabs 50 may have different respective transverse lengths L.

In other cases, the number of crown elements 30 may be 3 or higher. Also, in other cases, the number of tabs 50 may be more than three or fewer than three. Also, the number of the crown elements 30 may be an even number, and the number of the tabs 50 may be an odd number, or vice versa. In other cases, both the number of crown elements 30 and the number of tabs 50 may be even numbers. In further cases, both the number of crown elements 30 and the number of tabs 50 may be odd numbers.

Also, in some cases, a ratio that is the number of crown elements 30 divided by the number of tabs 50 may be a non-integer. For example, in the case in which the number of crown elements 30 is eight, and the number of tabs 50 is three, the ratio is 8/3=2.67. In other cases, the ratio that is the number of crown elements 30 divided by the number of tabs 50 may be an integer.

In some cases, the coupling of the tabs 50 to the crown elements 30 may be achieved by mechanical connectors, e.g., welds, adhesive, etc. In other cases, the coupling of the tabs 50 to the crown elements 30 may be achieved by integrally forming the tabs 50 with the crown elements 30.

In some cases, the porosity of the stent 12 is between fifty and ninety-five percent (50-95%) when the stent 12 is in the expanded configuration. In other cases, the porosity of the stent 12 may be lower than 50% or higher than 95% when the stent 12 is in the expanded configuration.

Figure 4A:
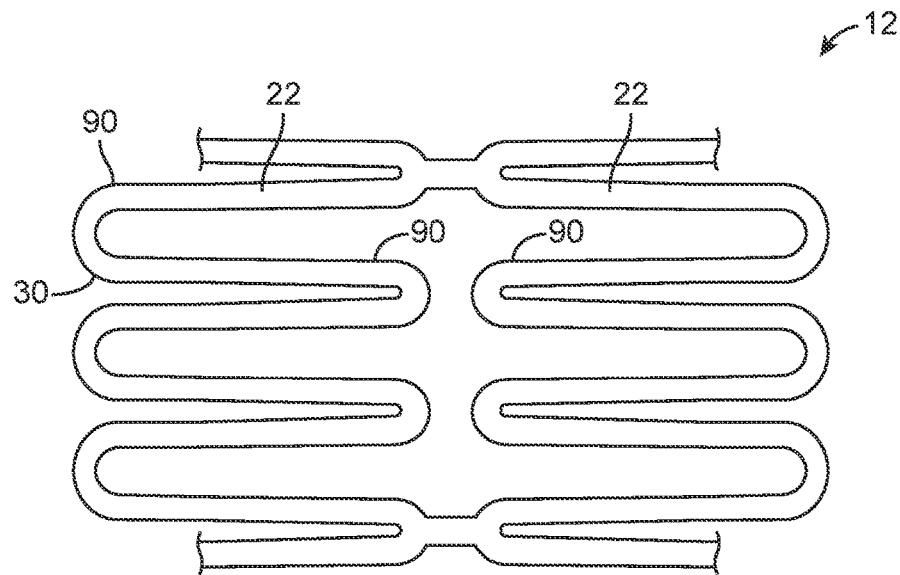
FIG. 4A illustrates elongate portions of the stent of FIG. 1 or FIG. 3A in accordance with some cases.

FIG. 4A illustrates elongate portions 22 of the stent 12 of FIG. 1 or FIG. 3A. As shown in FIG. 4A, an elongate portion 22 may have bend 90 with very small radius of curvature. This configuration results in a bend that has a "sharp-turning" profile, and may pose several issues. First, if the stent 22 is bent or twisted while it is inside a vessel, the "sharp" bend of the elongate portion 22 may stick out, and may lead to vessel damage. In the case where the elongate portion 22 is at the end of the stent (forming the crown elements 30), the "sharp" bend of the elongate portion 22 (or of the crown element 30) may provide a high level of localized pressure that may lead to vessel damage or pain (e.g., headache). In some cases, the twisting of the bend 90 may make the stent 12 go off the plane and may contribute to the additional point force that could lead to vessel damage or pain. In addition, the peak of the bend 90 is a place where strut fracture may occur due to stress concentration. Furthermore, the bends 90 may get misaligned during delivery, causing some of the bends 90 to be jammed and trapped in the space between other bends 90 facing the bends 90. This may result in the stent 12 being in a crimped state.

Figure 4B:
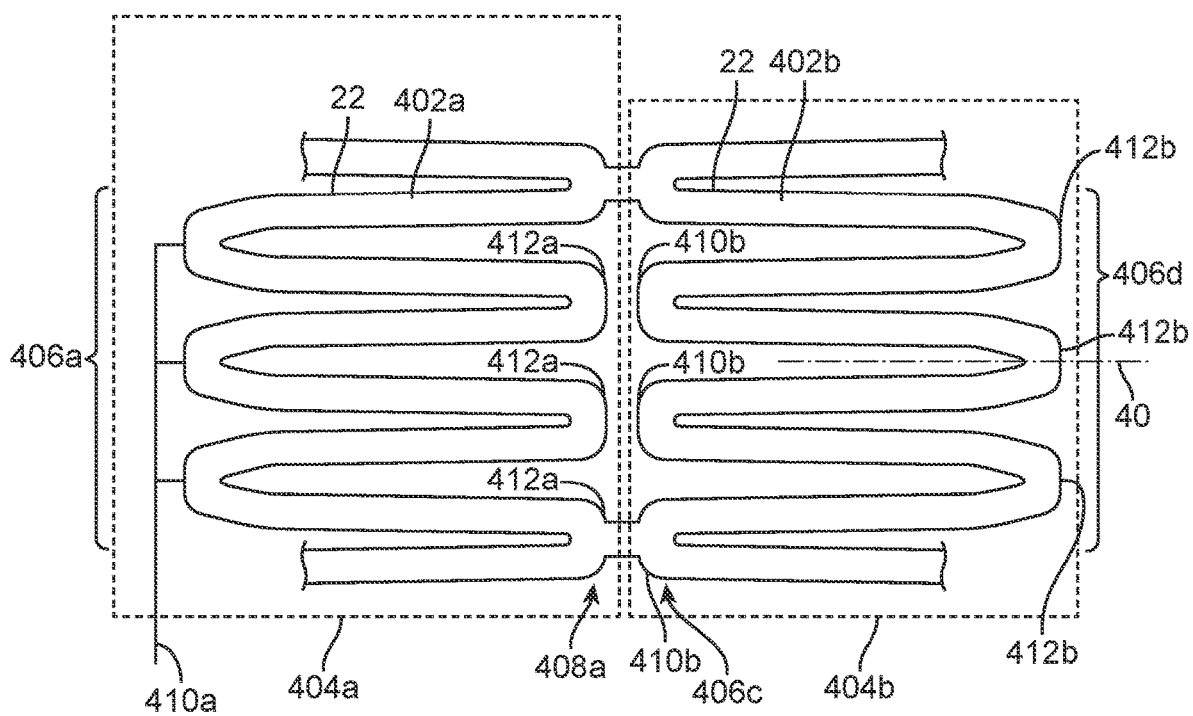
FIG. 4B illustrates elongate portions of the stent of FIG. 1 or FIG. 3A in accordance with other cases.

FIG. 4B illustrates elongate portions 22 of the stent 12 of FIG. 1 or FIG. 3A in accordance with other cases. As shown in FIG. 4B, the elongate portions 22 comprise a first zigzag portion 402*a* forming a first ring element 404*a*, the first ring element 404*a* having a first ring end 406*a*, and a second ring end 408*a* opposite from the first ring end 406*a*, wherein the first ring end 406*a* of the first ring element 404*a* has a first set of peaks 410*a* disposed circumferentially around the longitudinal axis 40 of the tubular structure 14, and wherein the second ring end 408*a* of the first ring element 404*a* has a second set of peaks 412*a* disposed circumferentially around the longitudinal axis 40 of the tubular structure 14. As shown in the figure, the peaks 410*a* in the first set are flat or are rectilinear. Thus, the peaks 410*a* are "flat" bends. Similarly, the peaks 412*a* in the second set are also flat or are rectilinear. Thus, the peaks 412*a* are "flat" bends.

As shown in FIG. 4B, the elongate portions 22 also comprise a second zigzag portion 402*b* forming a second ring element 404*b*, the second ring element 404*b* having a first ring end 406*c* and a second ring end 406*d* opposite from the first ring end 406*c* of the second ring element 404*b*, wherein the first ring end 406*c* of the second ring element 404*b* has a set of peaks (flat bends) 410*b* disposed circumferentially around the longitudinal axis 40 of the tubular structure 14. The peaks 410*b* of the second ring element 404*b* are flat or are rectilinear. In some cases, the set of peaks 410*b* of the second ring element 404*b* faces towards the second set of peaks 412a of the first ring element 404a. The second ring element 404b also has a set of peaks (flat bends) 412b disposed circumferentially around the longitudinal axis 40 of the tubular structure 14. The peaks 412b are located at the second ring end 406d of the second ring element 404b. The peaks 412b of the second ring element 404b are flat or are rectilinear.

The "flat" bends shown in FIG. 4B are advantageous. First, if the stent 22 is bent or twisted while it is inside a vessel, the "flat" bend of the elongate portion 22 may not stick out (or at least may not stick out as much compared to the sharp bend), thus preventing injury of vessel wall. In the case where the elongate portion 22 is at the end of the stent (forming the crown elements 30), the "flat" bend of the elongate portion 22 (or of the crown element 30) may provide a much lower level of localized pressure (compared to that of the sharp bend), thus also preventing injury of vessel wall. In addition, the "flat" bend feature reduces stress concentration due to the increased area at the peak. As a result, stress concentration "migrates" away from the bend, and risk of fracture at the bend is reduced. Furthermore, even if the "flat" bends get misaligned during delivery, the bends will abut against the adjacent bens due to their flat profile. Accordingly, the bends will not to be jammed and trapped in the space between the opposite bends. Thus, flattened peak (tip) increases the stent's ability to track smoothly by vastly reducing the chance of peak slipping past each other during delivery. In addition, the "flat" bend configuration makes the peak less prone to bending. Less bending will result in less out of plane conditions and lower localized pressure at the peak. This, in turn, will lead to reduced probability of vessel damage and pain.

Figure 4C:
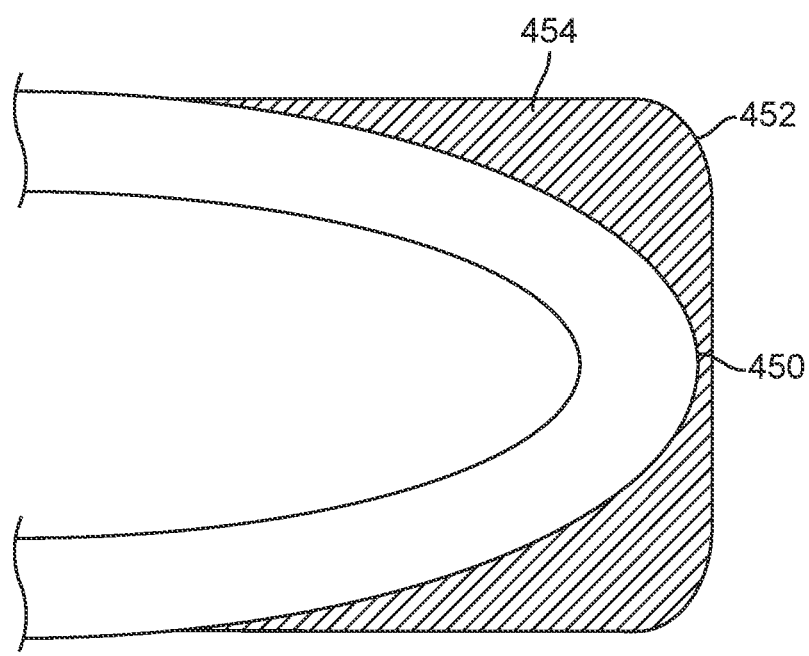
FIG. 4C illustrates a difference between a peak of a zig-zag portion of the stent of FIG. 4A and a peak of a zig-zag portion of the stent of FIG. 4B.

FIG. 4C illustrates a difference between a peak 450 of a zig-zag portion of the stent of FIG. 4A and a peak 452 of a zig-zag portion of the stent of FIG. 4B. As shown in FIG. 4C, the peak 450 and the peak 452 are superimposed to show an area difference 454 between the two peaks 450, 452. In some cases, the peak 452 may be formed by an elongate member, and the peak 450 (with the reference area against which the peak 452 is compared against) may be a reference peak formed only by hypothetically bending the elongate member. The area difference 454 is a difference between a surface area of the peak 450 and a surface area of the peak 452. As shown in the figure, the peak 452 provides the area difference 454 (increase in area) that extends both vertically and horizontally with respect to the reference peak 450. In some cases, the "flat" bend may provide at least 20% or more (e.g., up to 30% or more than 30%) surface area compared to existing peaks (e.g., reference peak). Accordingly, any localized force imposed on the peak, when normalized over the additional area, will result in less localized pressure at the peak (e.g. at least 20% localized pressure reduction). This will reduce risk of damage to vessel wall and pain.

In some cases, the "flat" bend may be achieved by using a larger crimped size when making the zigzag portions 402. Alternatively, a mandrel with a flat portion (e.g., a rectilinear surface or a surface with a large radius of curvature) may be used to make the zigzag portions 402.

Figure 5:
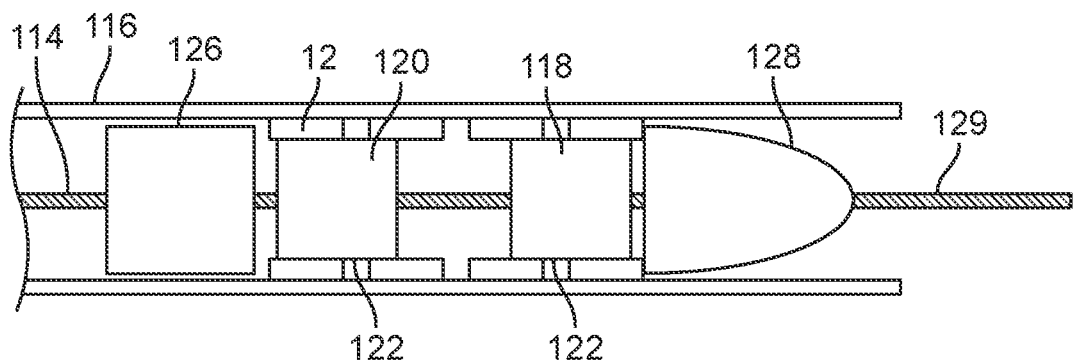
FIG. 5 is a partial cross-sectional view of an assembly that includes the stent of FIG. 1 and a delivery catheter.

In some cases, the stent 12 may be included with a delivery catheter that together form an assembly. FIG. 5 shows an assembly 110 that includes a delivery catheter 116, and the stent 12. The stent 12 is disposed between a guidewire 114 and the delivery catheter 116. The guidewire 114 may be a separate device from the delivery catheter 116, or may be considered as a part of the delivery catheter 116. The stent 12 is a self-expanding stent, and is contained in the delivery catheter 116, which constrains stent 112 from expanding into its fully-expanded state. A first seating member 118 and a second seating member 120 are disposed on the guidewire 114 between the guidewire 114 and the stent 12. The first and second seating members 118 and 120 each have a diameter such that seating surfaces 122 on each of the first and second members 118 and 120 contacts the stent 12 while the stent 12 is disposed within the delivery catheter 116. The seating members 118 and 120 are configured, in conjunction with the configurations of the stent 12 and the delivery catheter 116, such that, when the stent is disposed on the seating members 118 and 120 and is disposed within the delivery catheter 116, the stent 12 will preferentially remain disposed on the seating members 118 and 120 when catheter 116 and seating members 118 and 120 are moved with respect to each other. In some cases, the delivery catheter 116 may optionally further include an inner tube that includes a tube lumen for accommodating the guidewire 114. In such cases, the seating members 118, 120 may be fixedly coupled to the inner tube (e.g., the seating members 118, 120 may be mechanically connected to the inner tube, or may be formed together with the inner tube). In certain cases, this may be the result of a friction fit created by the contact between the stent 12 and the seating members 118 and 120. For example, the seating surfaces 122 may have a coefficient of friction higher than that of the inner surface of the delivery catheter 116. In certain cases, the seating members 118 and 120 and/or the seating surfaces 122 may be formed of a material which is at least partially deformable, for example, a soft, tacky, resilient, or elastomeric material, for example, a material having a durometer of from about 55 A to about 100 A (e.g., from about 60 A to about 90 A, from about 65 A to about 85 A, or from about 70 A to about 80 A) and/or from about 15 D to about 55 D (e.g., from about 20 D to about 50 D, from about 25 D to about 45 D, or from about 30 D to about 40 D). The durometer, or hardness, is measured in accordance with ASTM 2240. In some cases, the stent 12 is at least slightly pressed into the at least partially deformable seating member and/or seating surface. Exemplary materials include rubber, synthetic rubber, latex, polyurethane/silicone combinations such as, for example, Elast-Eon™ polymers by AorTech, and other polymers such as, for example, [poly(styrene-b-. isobutylene-b-styrene)] ("SIBS"), or poly-(ether block amide), (e.g., PEBAX®).

In certain cases, the seating surface may have one or more grooves into which the stent can be at least partially deployed. The stent 12, as a result of the seating members and/or seating surfaces, remains stationary with respect to the guidewire 114 when the delivery catheter 116 moves proximally or distally with respect to the guidewire 114. Likewise, while when the guidewire 114 moves proximally or distally, the stent 112 remains stationary with respect to the guidewire 114. Exemplary materials for forming the seating members 118 and 120 and/or the seating surfaces 122 include rubber, synthetic rubber, latex, polyurethane/silicone combinations such as, for example, Elast-Eon™ polymers, and other polymers such as, for example, [poly(styrene-b-. isobutylene-b-styrene)] ("SIBS"), or poly-(ether block amide), (e.g., PEBAX®). The seating surfaces 122 may be formed of the same or a different material than the seating members 118, 120, and may make up an additional layer or component of the seating members 118, 120 or may simply be the outer surface of each seating member rather than an additional component.

As illustrated in FIG. 5, the implantable medical endoprosthesis delivery system 110 may further include a proximal bumper 126 disposed on the guidewire 114 proximal to the stent 12. The proximal bumper 126 is configured to prevent proximal movement of the stent 12 when the delivery catheter 116 is moved proximally. The proximal bumper 126 may also serve to help in pushing the stent 12 through the delivery catheter 116 where such is desired. In some cases, the proximal bumper 126 may be implemented as a part of a plunger. A bullet-shaped tip 128 is connected to the guidewire 114 distal of the stent 12. The tip 128 is configured to prevent distal movement of the stent 12 when the delivery catheter 116 is moved distally and to assist in the delivery of the delivery catheter 116, preloaded with the stent 12, through body lumens to the position at which the stent 12 is to be deployed. Optionally, the guidewire 114 can extend through the tip 128 such that a distal portion 129 of the guidewire 114 extends beyond the tip 128 distally, for example, through a lumen (not illustrated) in the tip 128.

Figure 6A:
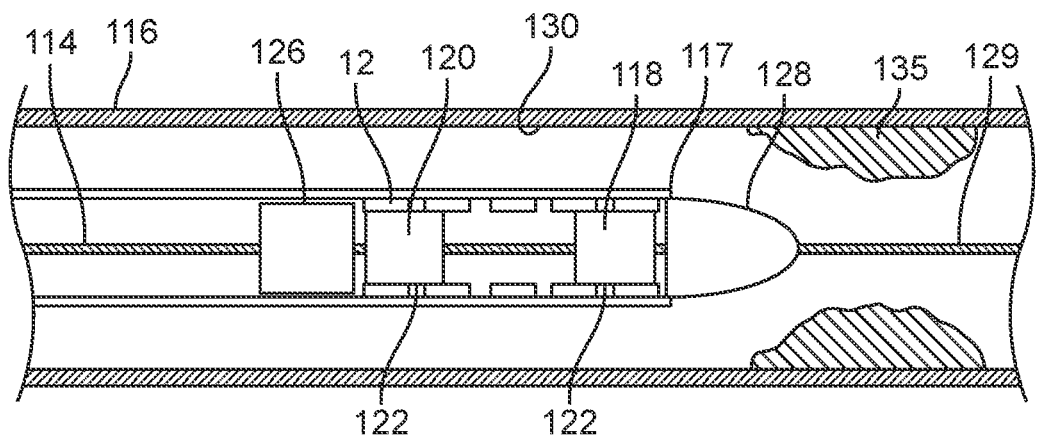
FIGS. 6A-6C are diagrams of a method.
Figure 6B:
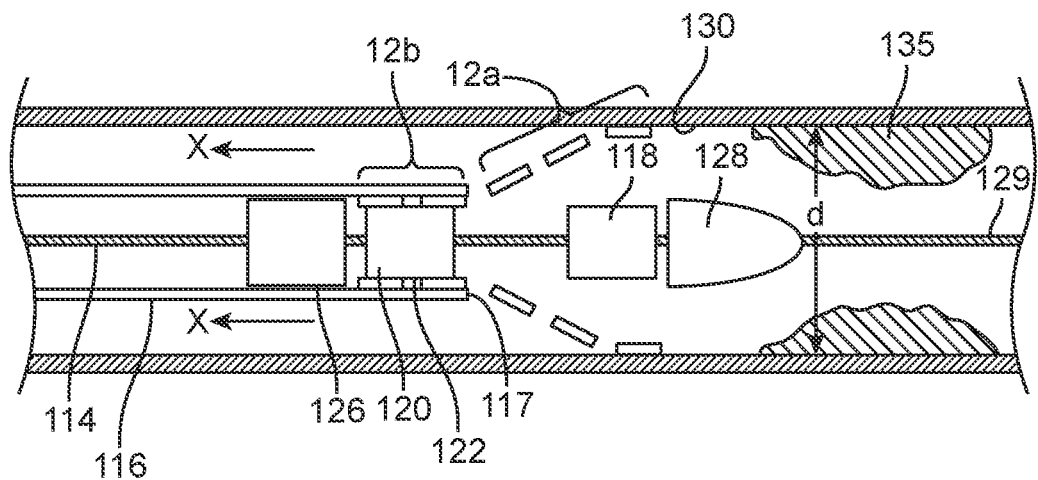
Figure 6C:
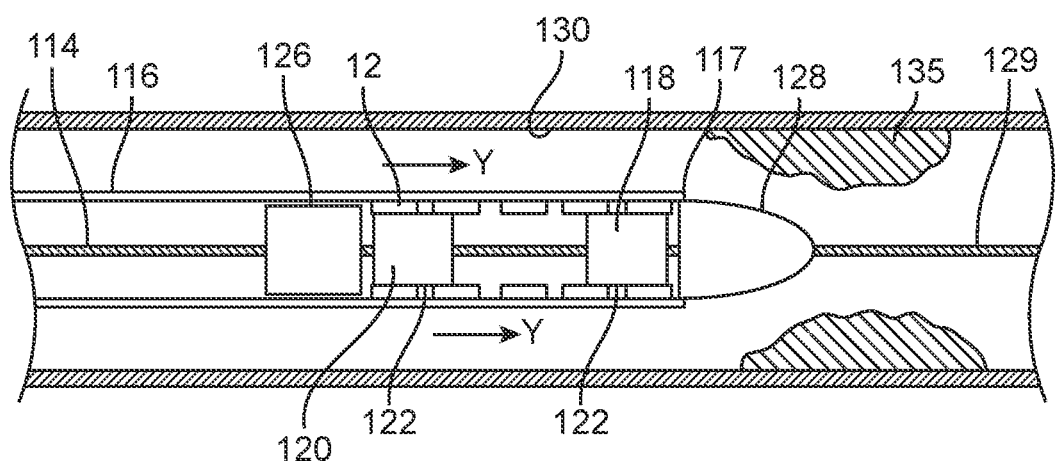
Figure 7A:
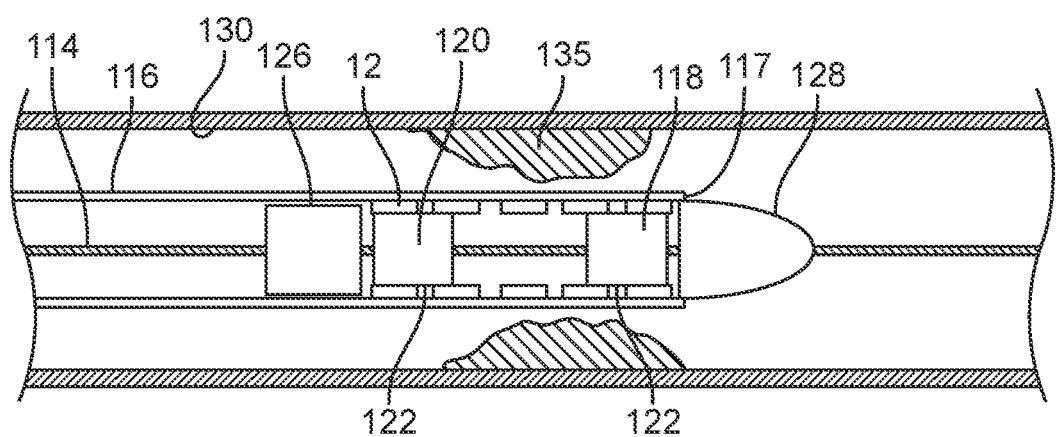
FIGS. 7A-7C are diagrams of a method.
Figure 7B:
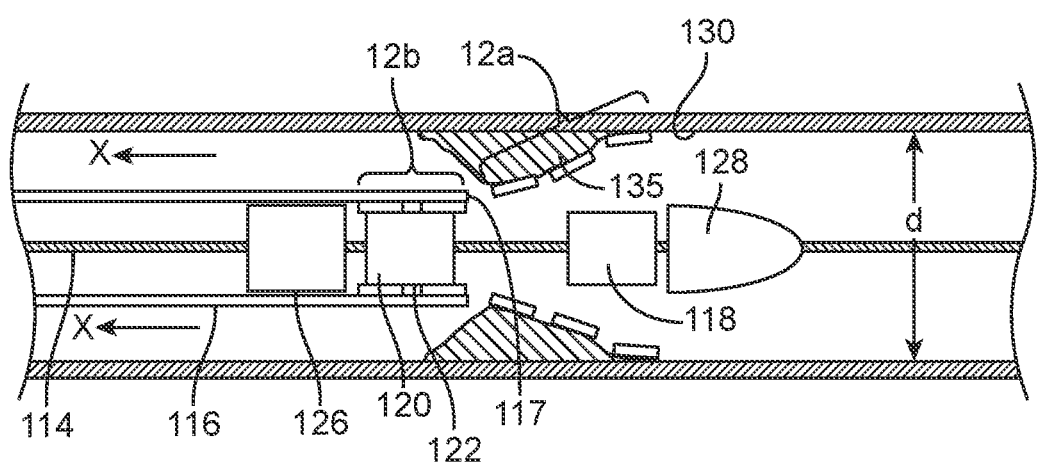

FIGS. 6 and 7 illustrate a method utilizing implantable medical endoprosthesis delivery system 110. In general, implantable medical endoprosthesis delivery system 110 is used as follows. System 110 is positioned within a body lumen 130 (e.g., an artery) at a desired location, for example, adjacent an occlusion 135. Initially, as seen in FIGS. 6A and 7A, the stent 12 is contained in an unexpanded state within the delivery catheter 116 at a distal end 117 of the delivery catheter 116. The delivery catheter 116 serves to restrain the stent 12 from self-expanding at this point. The delivery catheter 116 is withdrawn (moved proximally) as indicated by arrows X in FIGS. 6B and 6C, to expose or uncover a distal portion 112a of the stent 12. When the distal portion 112a of the stent 12 is uncovered (and thereby unrestrained from self-expansion), the distal portion self-expands towards a deployed diameter d, which is the diameter of the stent 12 when expanded in the body lumen 130. Typically, the deployed diameter d is less than the diameter to which the stent 12 would expand absent the body lumen 130. In this fashion, the stent 12 can continue to exert radial force, which can help to force open the occlusion and/or to maintain the position of the stent 12 within the body lumen 130.

At this point, the physician may desire to reposition the stent and/or system within lumen 130, e.g., to select a more suitable location for the stent or to correct for errors in positioning resulting from the partial deployment of the stent. Optionally, the physician may desire to entirely re-sheath and/or remove the stent (e.g., to replace it with a stent of, for example, a larger or smaller expanded diameter). Re-sheathing of the stent is possible, due at least in part to the presence of the second seating member 120. The delivery catheter 116 can, as illustrated in FIG. 6C, be advanced (moved distally as indicated by arrows Y) to re-cover at least some of the expanded distal portion 112a of the stent 12 and depose the at least some of the expanded distal portion 112a of the stent 12 within the delivery catheter 116.

Figure 7C:
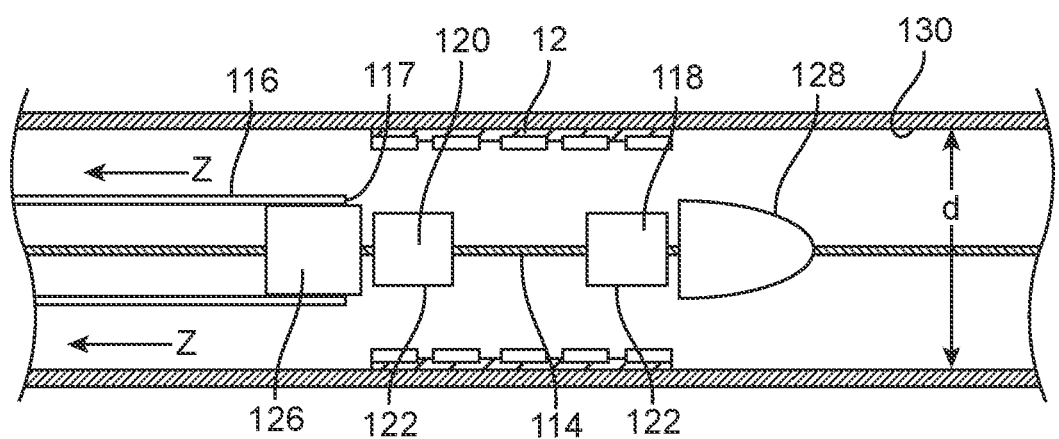

Alternatively, as illustrated in FIG. 7C, the delivery catheter 116 can be further withdrawn as indicated by arrows Z to expose or uncover the remaining proximal portion 112b of stent 12. Stent 12 can expand to the extent that the body lumen 130 permits once so exposed.

Figure 8A:
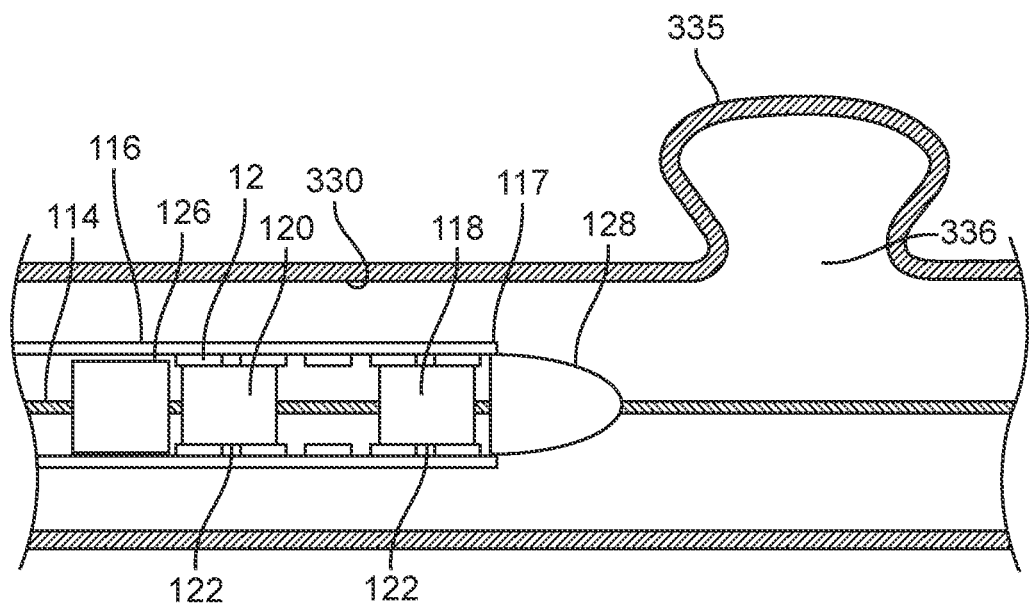
FIGS. 8A-8C are diagrams of a method.
Figure 8B:
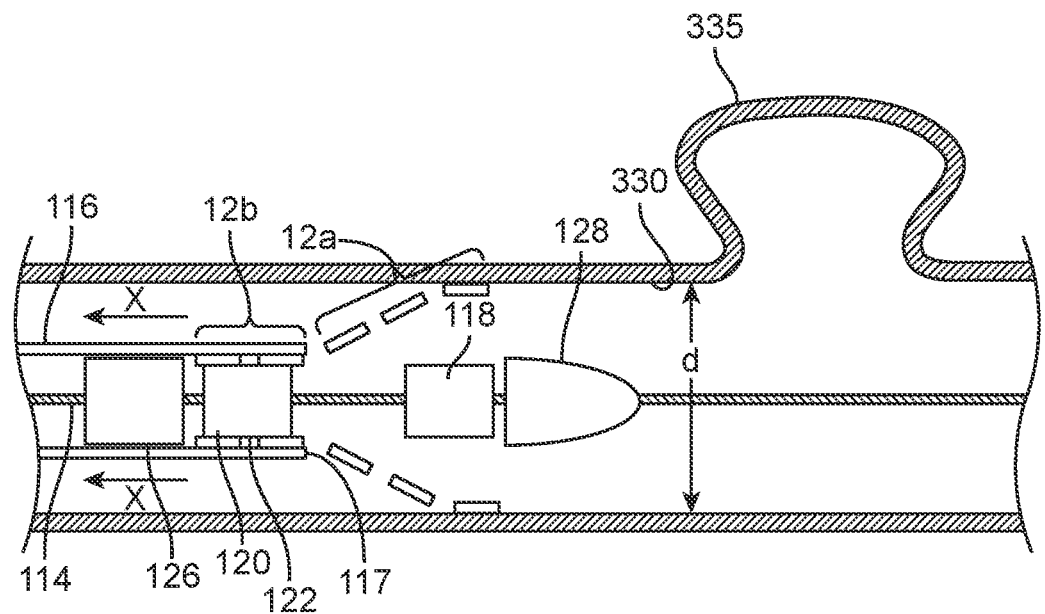
Figure 8C:
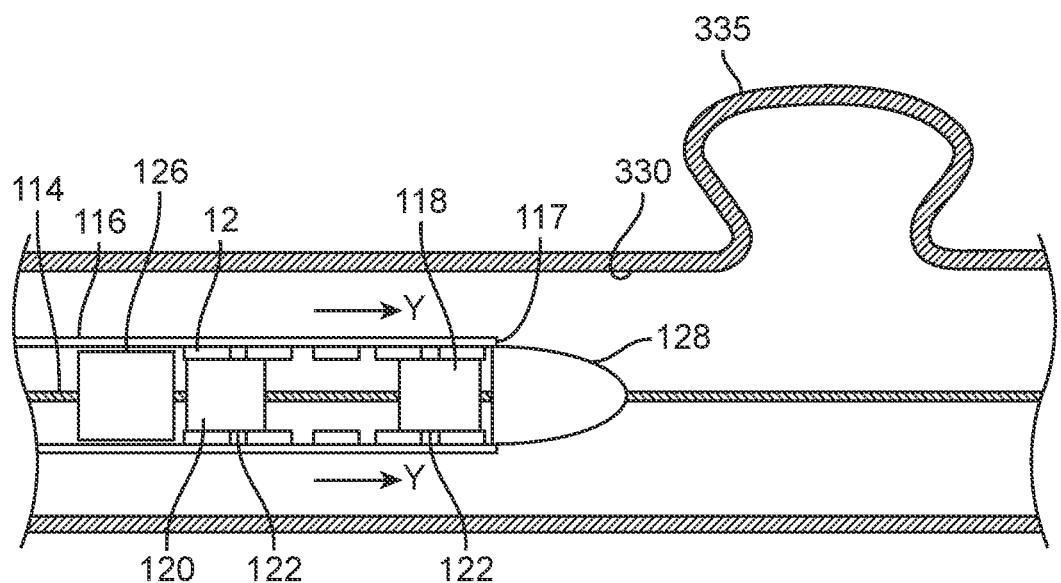
Figure 9A:
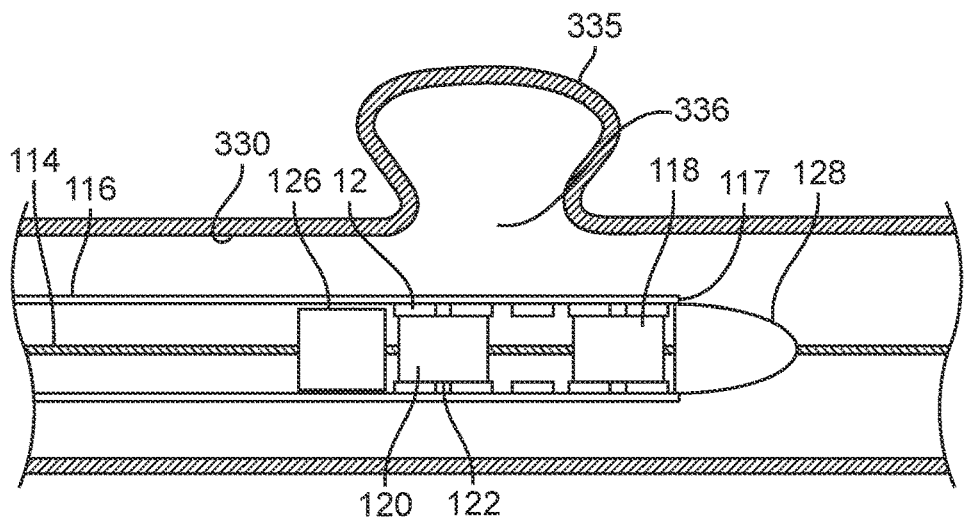
FIGS. 9A-9C are diagrams of a method.
Figure 9B:
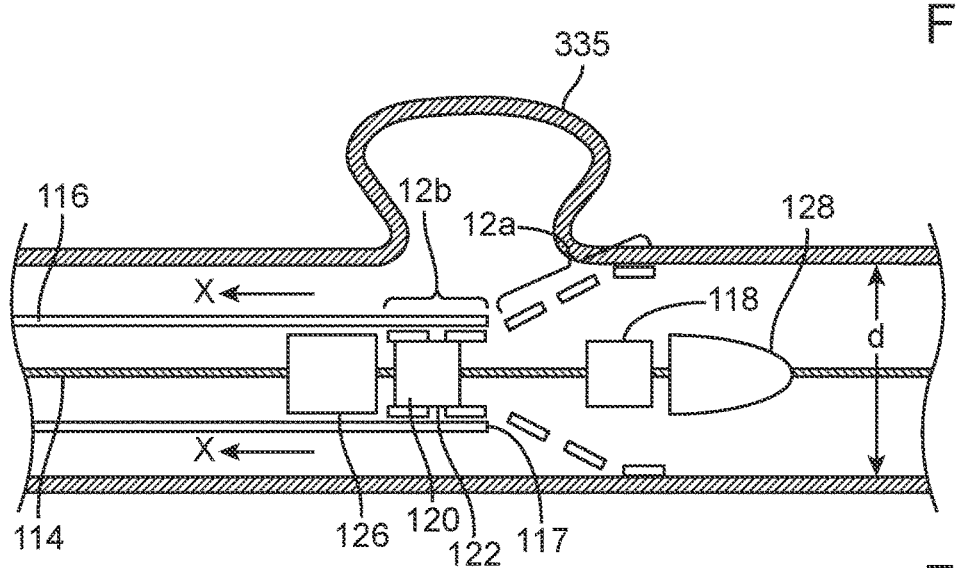

FIGS. 8 and 9 illustrate a similar method, utilizing implantable medical endoprosthesis delivery system 110 to block the opening of an aneurysm 335 and/or strengthen a vessel at the site of aneurysm 335. System 110 is positioned within a body lumen 330 (e.g., an artery) at a desired location, for example, adjacent aneurysm 335. Initially, as seen in FIGS. 8A and 9A, the stent 12 is contained in an unexpanded state within the delivery catheter 116 at a distal end 117 of the delivery catheter 116. The delivery catheter 116 is withdrawn (moved proximally) as indicated by arrows X in FIGS. 8B and 9B, to expose or uncover a distal portion 112a of the stent 12. When the distal portion 112a of the stent 12 is uncovered (and thereby unrestrained from self-expansion), the distal portion self-expands towards a deployed diameter d, which is the diameter of the stent 12 when expanded in the body lumen 330. At this point, the physician may desire to reposition the stent and/or system within lumen 330 or to entirely re-sheath and remove the stent and replace it with a stent of, for example, a larger or smaller expanded diameter. The delivery catheter 116 can, as illustrated in FIG. 8C, be advanced (moved distally as indicated by arrows Y) to re-cover at least some of the expanded distal portion 112a of the stent 12 and depose the at least some of the expanded distal portion 112a of the stent 12 within the delivery catheter 116.

Figure 9C:
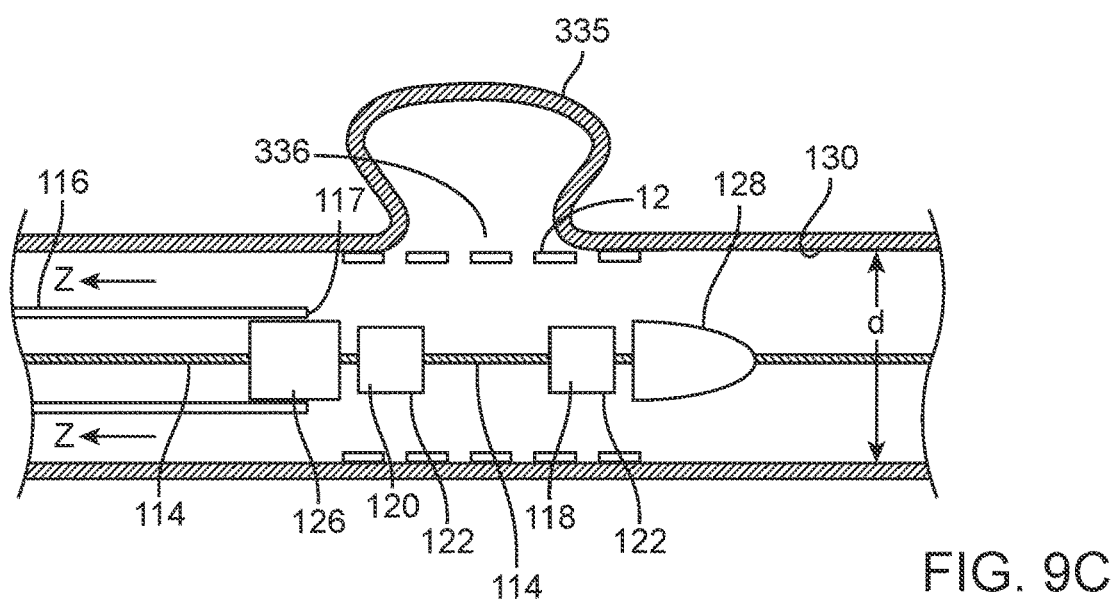

Should the physician determine that the stent 12 is properly positioned within lumen 330, as illustrated in FIG. 9C, the delivery catheter 116 can be further withdrawn as indicated by arrows Z to expose or uncover the remaining proximal portion 112b of stent 12. Stent 12 can then expand to the extent that the body lumen 330 permits once so exposed, thereby at least partially occluding the opening 336 to the aneurysm 335.

Figure 10:
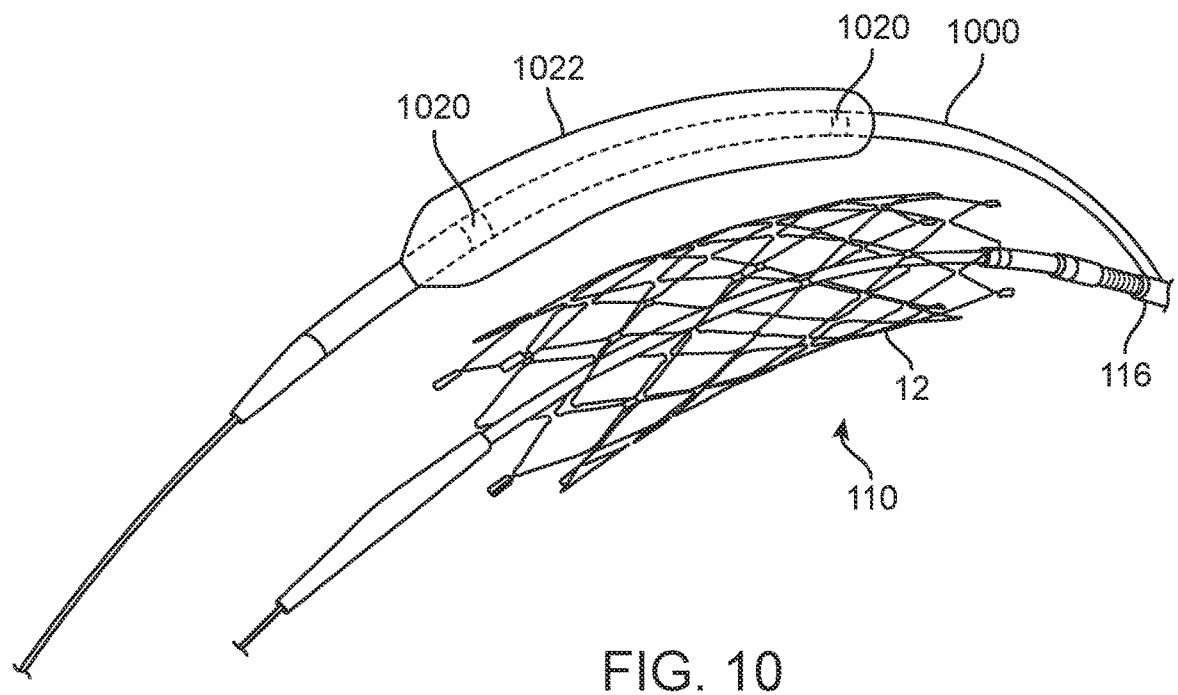
FIG. 10 illustrates a system that includes a balloon catheter, and the assembly of FIG. 1.

In some cases, the assembly 110 may be provided with a balloon catheter, which together form a system. FIG. 10 illustrates a system that includes a balloon catheter 1000, and an assembly 110 that includes the stent 12 and the delivery catheter 116. The stent 12 is the same as that described previously with reference to FIGS. 1-4. Also, the delivery catheter 116 is the same as that described with reference to FIG. 1. The balloon catheter 1000 includes a balloon 1022 configured to press against lesion that is located in a vessel, and markers 1020 for assisting placement and positioning of the balloon catheter 1000.

Figure 11A:
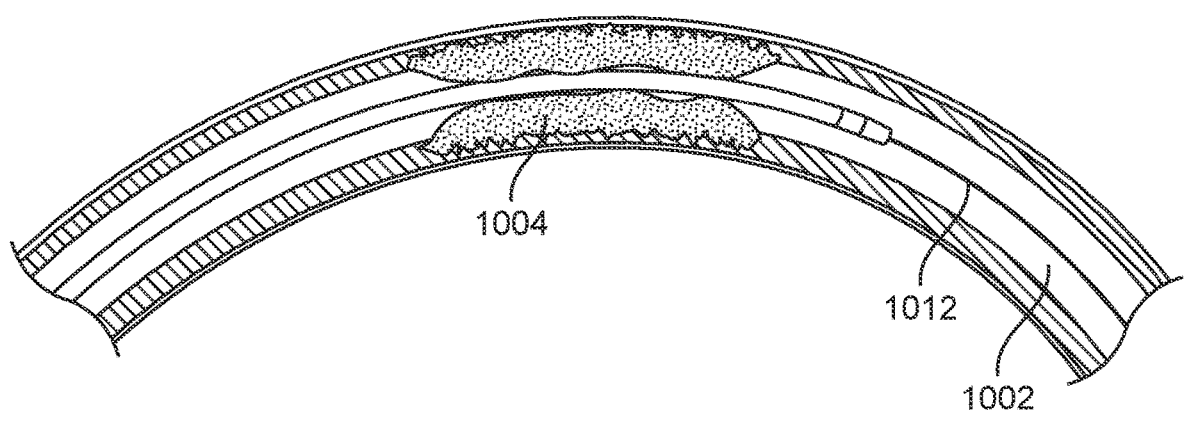
FIGS. 11A-11L illustrate a method of using the system of FIG. 10.
Figure 11B:
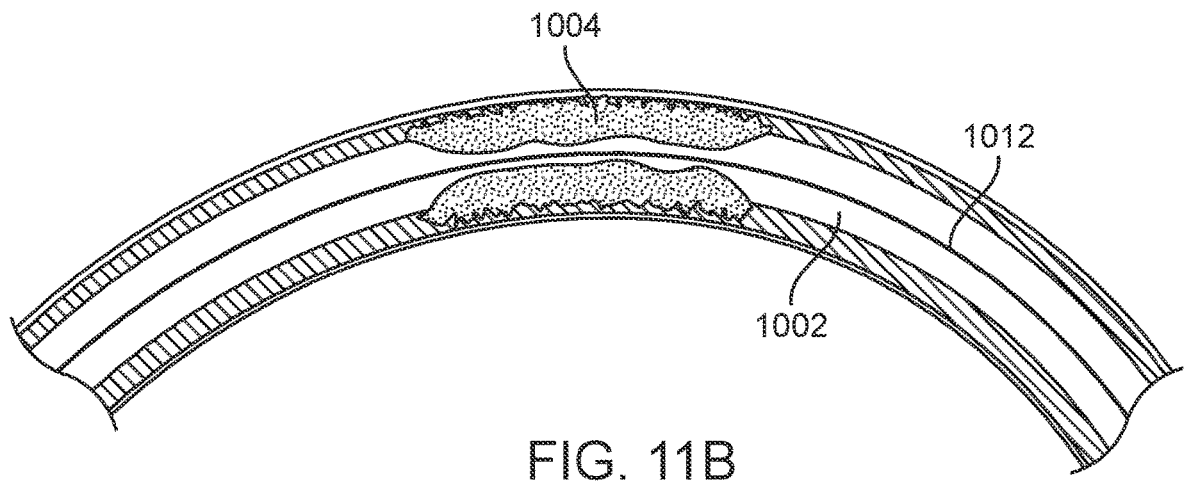
Figure 11C:
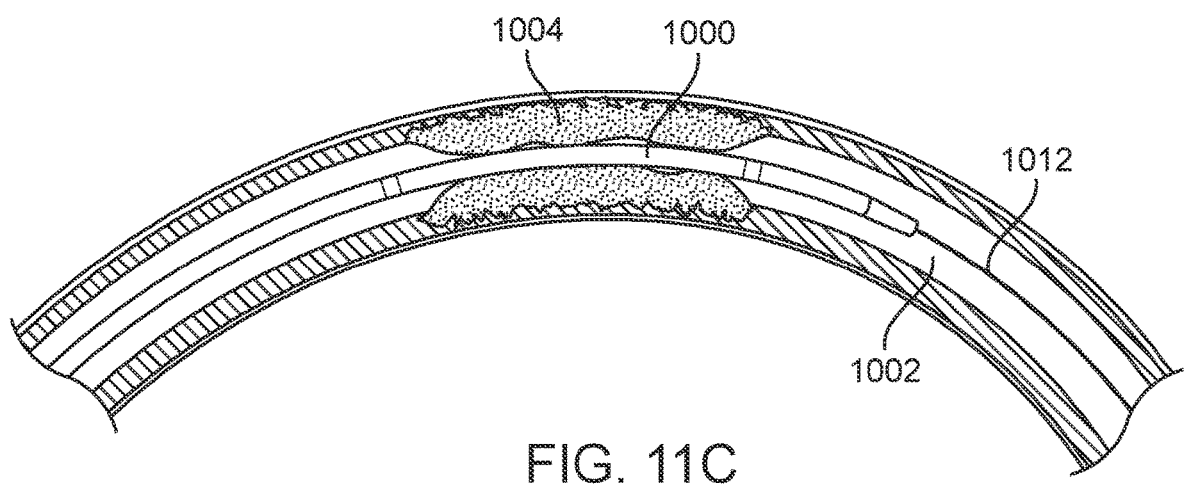
Figure 11D:
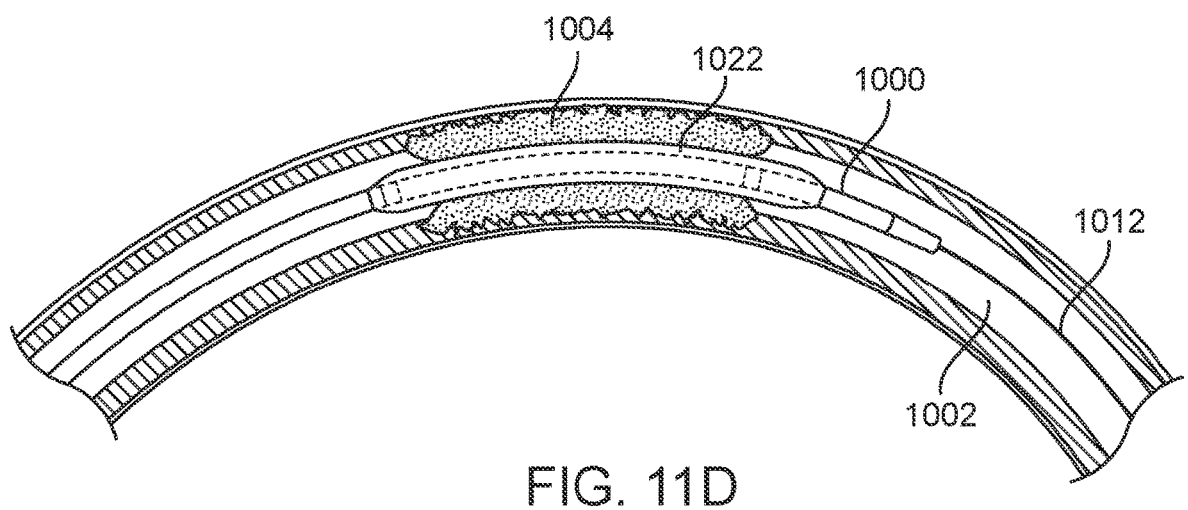
Figure 11E:
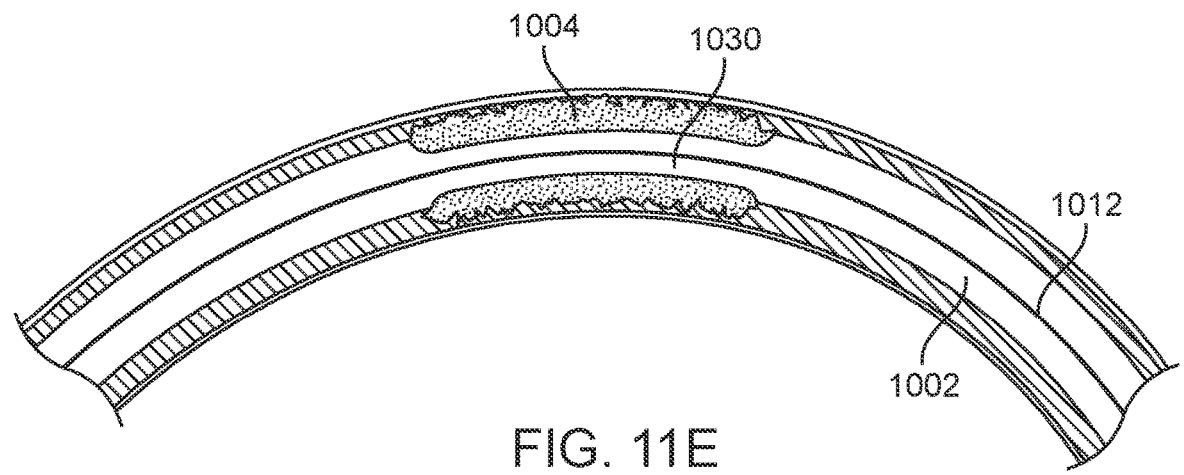

FIGS. 11A-11L illustrate a method of using the system 1000 of FIG. 10. In particular, the system 1000 may be used to treat a clogged vessel. Referring to FIG. 11A, to treat a vessel 1002 with a lesion 1004, a microcatheter 1010 is used to access the vessel 1002, and a guidewire 1012 may be delivered into the vessel 1002 and advanced to the location of the lesion 1004 via the microcatheter 1010. As shown in the figure, the guidewire 1012 is advanced until the distal end of the guidewire 1012 has passed the lesion 1004. Next, the microcatheter 1010 may be removed from the vessel (FIG. 11B). Then the balloon catheter 1000 is inserted into the vessel 1002 and is advanced over the guidewire 1012 (FIG. 11C). The balloon catheter 1000 is advanced until the catheter 1000 has reached the lesion 1004. The markers 1020 of the balloon catheter 1000 may be employed to assist placement of the balloon catheter 1000. As shown in the figure, the balloon catheter 1000 is positioned relative to the lesion 1004 such that the markers 1020 are near opposite ends of the lesion 1004. After the balloon catheter 1000 is desirably positioned in the vessel 1002, the balloon 1022 on the balloon catheter 1000 is then inflated (FIG. 11D). The balloon 1022 expands radially in response to the inflation, and presses the lesion 1004 radially outward towards the vessel wall. As a result, the lesion 1004 is compressed, leaving a passageway 1030 extending through the lesion 1004 (FIG. 11E).

Figure 11F:
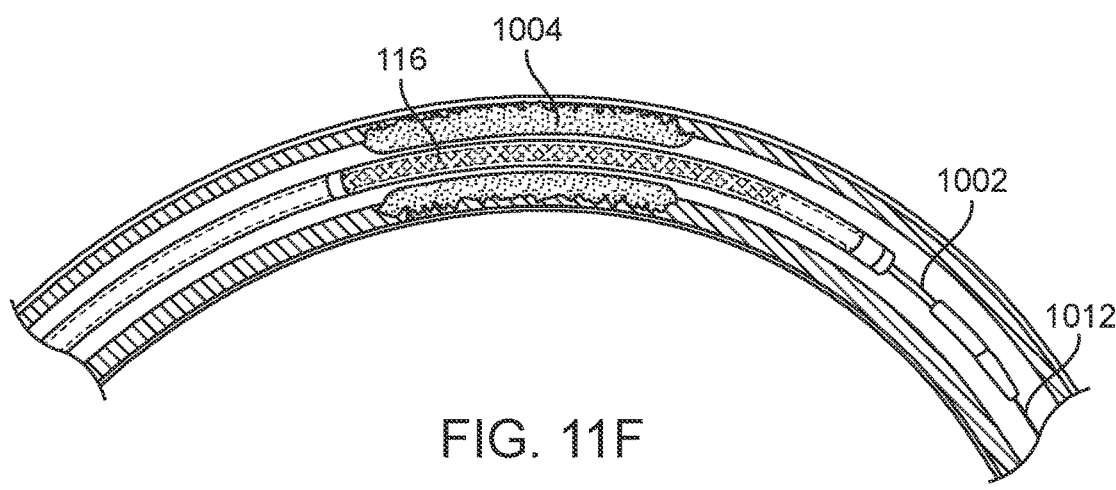

Referring now to FIG. 11F, after the balloon catheter 1000 is removed from the vessel 1002, the delivery catheter 116 of the assembly 110 may then be inserted into the vessel 1002, and may be advanced over the guidewire 1012. The delivery catheter 116 is positioned relative to the vessel 1002 such that the stent 12 is aligned with the lesion 1004. In some cases, placement of the delivery catheter 116 may be assisted by markers 1080a, 1080b on the delivery catheter 116, and/or by the tabs 50 at opposite ends 16, 18 of the stent 12. In some cases, the delivery catheter 116 may be positioned so that the ends 16, 18 of the stent 12 are outside respective opposite ends of the lesion 1004. For example, the stent 12 may have a certain length and the delivery catheter 116 may be positioned, such that the first end 16 of the stent 12 is at least 1 mm, or more preferably at least 2 mm, and more preferably at least 3 mm, outside a first end of the lesion 1004, and such that the second end 18 of the stent 12 is at least 1 mm, or more preferably at least 2 mm, and more preferably at least 3 mm, outside a second end of the lesion 1004.

Figure 11G:
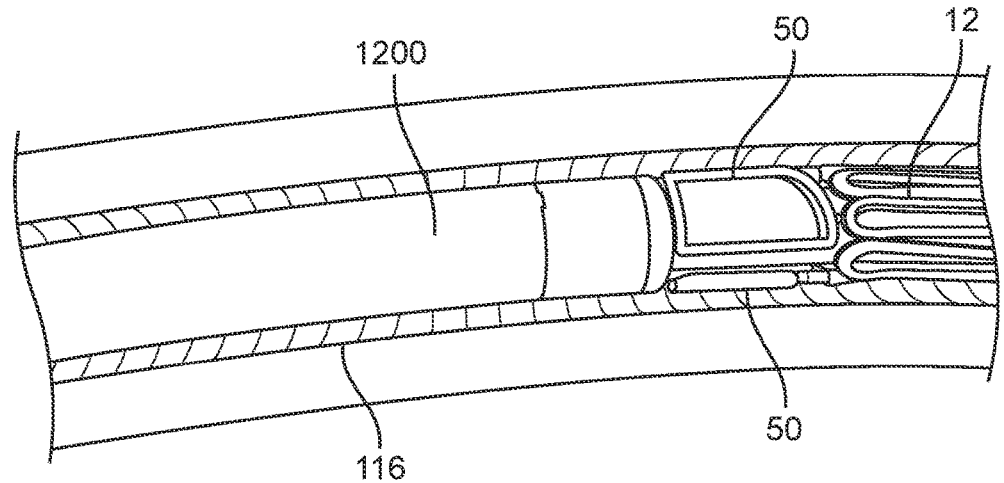
Figure 11H:
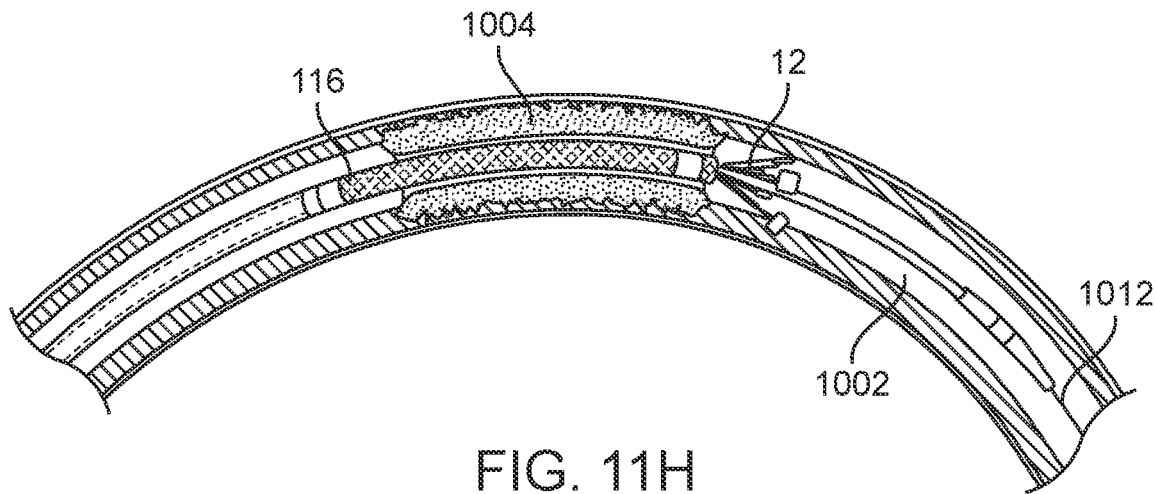
Figure 11I:
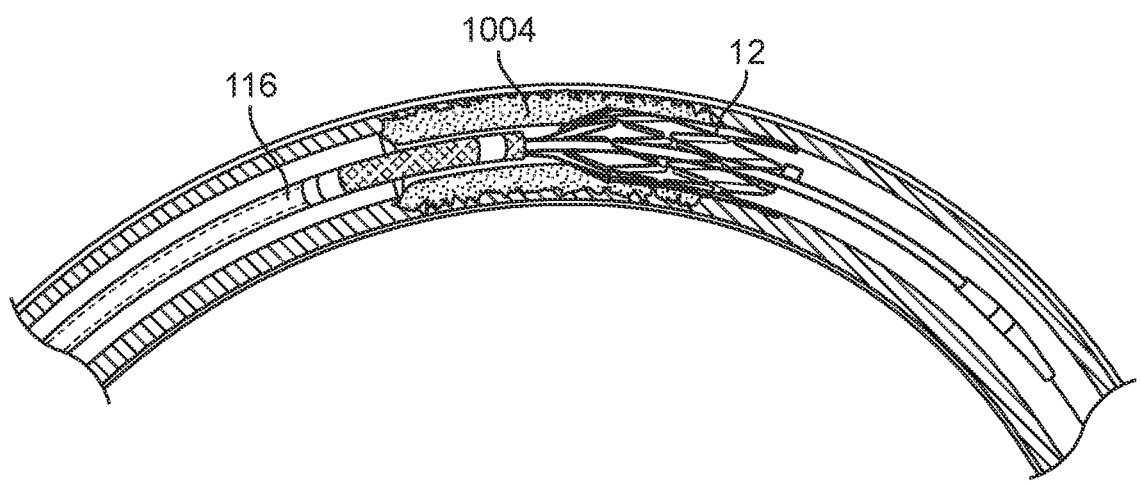
Figure 11J:
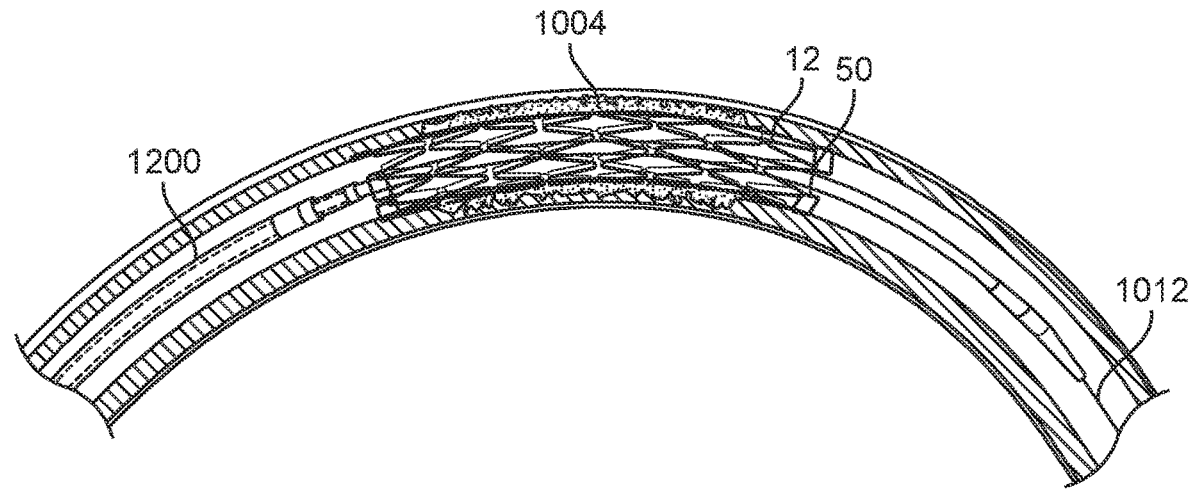
Figure 11K:
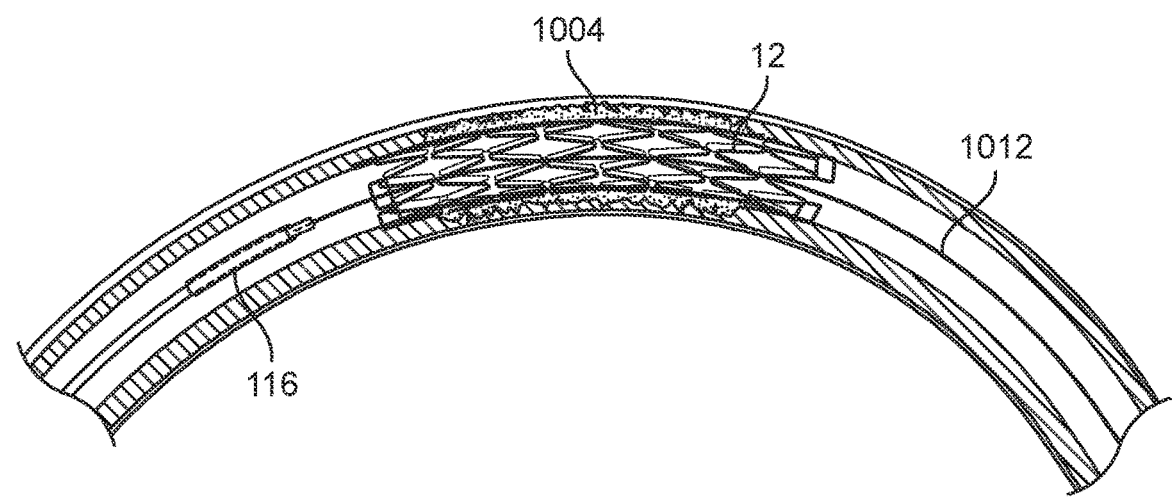

As shown in FIG. 11G, a plunger 1200 is in the delivery catheter 116 proximal to the stent 12. The plunger 1200 may be pre-loaded into the delivery catheter 116 before the delivery catheter 116 is placed inside the vessel 1002. Alternatively, the plunger 1200 may be placed inside the delivery catheter 116 after the delivery catheter 116 has been desirably positioned inside the vessel 1002. The plunger 1200 may be advanced until the distal end of the plunger 1200 abuts against a proximal tip of the stent 12. To deploy the stent 12 from the delivery catheter 116, the plunger 1200 is maintained in position relative to the vessel 1002 while the external sheath of the delivery catheter 116 is pulled proximally relative to the plunger 1200. Because the plunger 1200 prevents the stent 12 from moving in the proximal direction, as the sheath of the delivery catheter 116 is moved proximally, the distal portion of the stent 12 exits from the distal end of the delivery catheter 116 (FIG. 11H). As the delivery catheter 116 is moved further proximally, additional portion of the stent 12 following the distal portion exits from the distal end of the delivery catheter 116 (FIG. 11I). After the stent 12 is completely delivered outside the delivery catheter 116 (FIG. 11J), the delivery catheter 116 may then be removed from the vessel (FIG. 11K). Next, the guidewire 1012 is removed from the vessel (FIG. 11L).

Figure 11L:
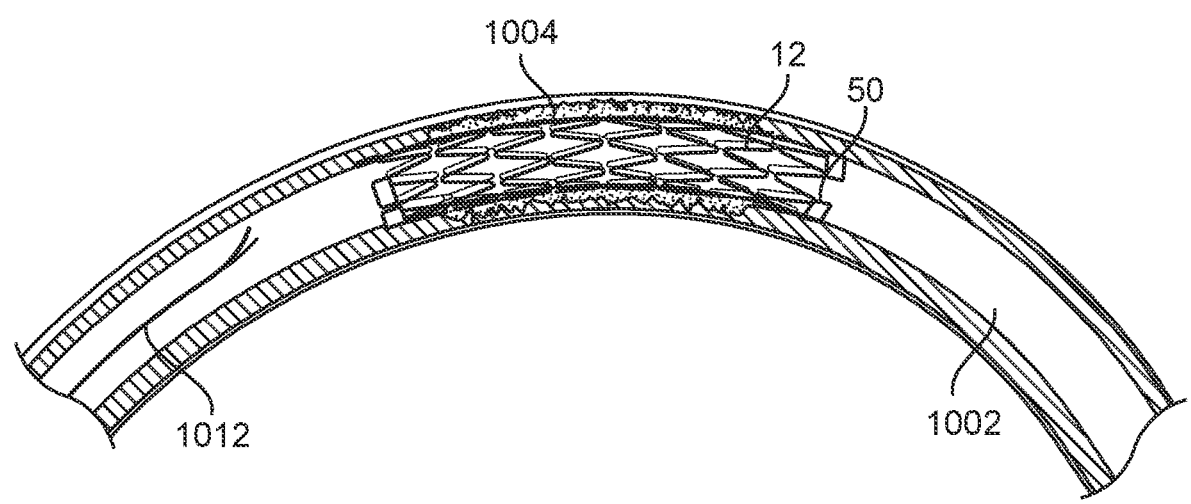

As shown in FIG. 11L, the delivered stent 12 provides a radial force to press against the lesion 1004 to maintain a passage way through the vessel 1002. Also, in some cases in which the stent 12 has the elongate members 22 of FIG. 4B, the "flat" bends of the elongate members 22 reduce the risks of injuring the vessel wall during and after placement of the stent 12. In addition, the "flat" bends of the elongate members 22 reduce the risk of the "flat" bends in one row being pushed into the spacing between the "flat" bends in the adjacent row. Also, the "flat" bends forming the crown elements 30 at the ends 16, 18 of the tubular structure prevents injury of the vessel wall during and after placement of the stent 12 as well. Furthermore, the tabs 50 allows visualization of the stent 12 during and after delivery of the stent, and also assist in preventing injury of the vessel wall due to the enlarged width of the tabs 50. Because the tabs 50 are disposed circumferentially with respect to the longitudinal axis 40 and move radially outward in response to the expansion of the stent 12, the tabs 50 remain close to the vessel wall after deployment of the stent 12 and do not impede blood flow through the vessel 1002.

It should be noted that the guidewire that can be used with the stent 12 is not limited to the examples described herein, and that other guidewires having other configurations may be used.

In addition, it should be noted that the term "flat", as used in this specification, refers to a profile that is straight (e.g., rectilinear), or approximately straight (e.g., a profile with a slight curvature). For example, when describing the bend formed by the elongate member 22 of the stent 12 as being "flat", such bend may have a slight curvature that is small enough to prevent the bend from injuring a vessel wall.

Also, as used in this specification, the term "about" refers to a variation of a value that is within 10%, unless specifically stated otherwise. For example, equal to or less than "about 10%" by weight refers to a weight that is 10%+/−1% of the total weight or less.

Although particular features have been shown and described herein, it will be understood by those skilled in the art that they are not intended to limit the claimed inventions, and it will be obvious to those skilled in the art that various changes, permutations, and modifications may be made (e.g., the dimensions of various parts, combinations of parts) without departing from the scope of the claimed inventions, which is to be defined only by the following claims and their equivalents. The specification and drawings are, accordingly, to be regarded in an illustrative rather than restrictive sense. The claims are intended to cover alternatives, modifications, and equivalents.

What is claimed is:

1. A stent configured for implantation in a body lumen, comprising:
    a tubular structure having a first end, a second end opposite from the first end, and a tubular body extending between the first end and the second end, the tubular structure having a longitudinal axis extending between the first and second ends, the tubular body comprising a plurality of elongate portions defining a porosity for the stent, at least one of the elongate portions having a zig-zag configuration, the first end of the tubular structure having a plurality of crown elements disposed circumferentially with respect to the longitudinal axis of the tubular structure, the crown elements forming a crown configuration for the first end of the tubular body; and
    a plurality of tabs coupled to the first end of the tubular structure, the tabs being disposed circumferentially with respect to the longitudinal axis of the tubular structure;
    wherein the tabs are configured to move radially away from the longitudinal axis of the tubular structure in correspondence with a radial expansion of the tubular structure;
    wherein a number of the crown elements is higher than a number of the tabs;
    wherein the tabs are coupled to only a subset, and not all, of the crown elements;
    wherein the stent has a delivery configuration when confined inside a delivery catheter, and wherein one of the tabs is coupled to one of the crown elements, wherein a first part of the one of the tabs is aligned with the one of the crown elements along a first axis that is parallel to the longitudinal axis when the stent is in the delivery configuration, and a second part of the one of the tabs is aligned with an adjacent one of the crown elements along a second axis that is parallel to the longitudinal axis when the stent is in the delivery configuration; and
    wherein the tabs comprise a first tab having a first structural side that is perpendicular to the longitudinal axis, and wherein one of the crown elements is coupled to the first structural side of the first tab at a location on the first structural side that is away from a center of the first structural side and that is away from opposite ends of the first structural side.

2. The stent of claim 1, wherein the number of the crown elements is 3 or higher.

3. The stent of claim 1, wherein the crown elements are the only crown elements at the first end of the tubular structure, wherein the number of the crown elements is a total number of all of the crown elements at the first end of the tubular structure, and wherein the total number of all of the crown elements at the first end of the tubular structure is 8, and the number of the tabs is 3.

4. The stent of claim 1, wherein the crown elements are the only crown elements at the first end of the tubular structure, wherein the tabs are the only tabs coupled to the first end of the tubular structure, wherein the number of the crown elements is a total number of all of the crown elements at the first end of the tubular structure, wherein the number of the tabs is a total number of all of the tabs coupled to the first end of the tubular structure, and wherein a ratio that is the total number of all of the crown elements divided by the total number of all of the tabs is a non-integer.

5. The stent of claim 1, wherein the number of the crown elements is an even number, and the number of the tabs is an odd number, or vice versa.

6. The stent of claim 1, wherein the tabs comprise marker tabs.

7. The stent of claim 1, wherein one of the crown elements comprises a bend of one of the elongate portions.

8. The stent of claim 1, wherein one of the tabs comprises a curvilinear structure, wherein the curvilinear structure is curved with respect to the longitudinal axis, and comprises a tab-opening defined by circumferential parts of the curvilinear structure.

9. The stent of claim 1, wherein the tabs are configured to circumferentially move apart from each other in correspondence with a radial expansion of the tubular structure.

10. The stent of claim 1, wherein the tabs comprise a second tab having a second structural side that is perpendicular to the longitudinal axis wherein another one of the crown elements is coupled to the second structural side of the second tab at a location on the second structural side that is away from a center of the second structural side.

11. The stent of claim 1, wherein the stent has an expanded configuration for implantation in the body lumen, and wherein the stent is biased to the expanded configuration.

12. The stent of claim 11, wherein the porosity of the stent is between fifty and ninety-five percent (50-95%) when the stent is in the expanded configuration.

13. The stent of claim 1, wherein the elongate portions comprise a first zigzag portion and a second zigzag portion.

14. The stent of claim 1, wherein one of the elongate portions comprises a zigzag portion forming a ring element, the ring element having a first ring end, and a second ring end opposite from the first ring end, wherein the first ring end has a first set of peaks disposed circumferentially around the longitudinal axis of the tubular structure, and wherein the second ring end has a second set of peaks disposed circumferentially around the longitudinal axis of the tubular structure.

15. The stent of claim 14, wherein the highest parts of the respective peaks in the first set are flat or are rectilinear.

16. An assembly comprising the stent of claim 1 and the delivery catheter, wherein the stent is located in a lumen of the delivery catheter.

17. The assembly of claim 16, further comprising a plunger located in the lumen of the delivery catheter, wherein the plunger is slidable relative to the delivery catheter, and is located proximal with respect to the stent.

18. The stent of claim 1, wherein the crown elements all lie in a same plane that is perpendicular to the longitudinal axis.

19. The stent of claim 1, wherein when the stent is in the delivery configuration, none of the crown elements is between two adjacent ones of the tabs.

20. The stent of claim 1, wherein the first structural side is a most-proximal side of the first tab.

* * * * *